(12) United States Patent
Dharmarajan et al.

(10) Patent No.: US 8,252,746 B2
(45) Date of Patent: Aug. 28, 2012

(54) ANTI-ANGIOGENIC AGENTS AND METHODS OF THEIR USE

(75) Inventors: Arunasalam Dharmarajan, Willetton (AU); Survo Chatterjee, Chennai (IN)

(73) Assignees: The University of Western Australia, Nedlands (AU); KBC Research Foundations Private Limited, Chennai (IN); Anna University, Chennai (IN)

( * ) Notice: Subject to any disclaimer, the term of this patent is extended or adjusted under 35 U.S.C. 154(b) by 240 days.

(21) Appl. No.: 12/285,713

(22) Filed: Oct. 10, 2008

(65) Prior Publication Data

US 2009/0170771 A1 Jul. 2, 2009

Related U.S. Application Data

(63) Continuation of application No. PCT/AU2007/000477, filed on Apr. 11, 2007.

(51) Int. Cl.
*A61K 38/00* (2006.01)
*A61K 38/16* (2006.01)
*A61K 35/12* (2006.01)

(52) U.S. Cl. .................. 514/13.3; 514/21.2; 424/198.1; 424/277.1

(58) Field of Classification Search .................... None
See application file for complete search history.

(56) References Cited

U.S. PATENT DOCUMENTS

2004/0247593 A1  12/2004 He et al.

OTHER PUBLICATIONS

Ngo et al., 1994, The Protein Folding Problem and Tertiary Structure Prediction, pp. 492-495.*
Wells, Aditivity of Mutational Effects in Proteins, 1990, Biochemistry, vol. 26, No. 37, pp. 8509-8517.*
Dufourcq et al. Circulation, 2002; vol. 106, pp. 3097-3103.*
Marsit, C.J. et al. 2005 Epigenetic inactivation of SFRP genes and TP53 Alteration Act Jointly as Markers of Invasive Bladder Cancer. Cancer Res. 65(16):7081-5.
Han Q.F. et al. (2006) Expression of sFRP-4 and β-catenin in human colorectal carcinoma; Cancer Letters 231:129-137.
Qui, Jian et al. (2006) Hypermethylation and expression regulation of secreted frizzled-related protein genes in colorectal tumor. World J. of Gastroenterology, 12(44):7113-7117.
Risenger J.I. et al. (2005) Gene Expression Profiling of Microsatellite Unstable and Microsatellite Stable Endometrial Cancers Indicates Distinct Pathways of Aberrant Signalling. Cancer Res. 2005; 65(12):5031-7.
Wissman C. et al. (2003) WIFI, a component of the Wnt pathway, is down-regulated in prostate, breast, lung, and bladder cancer. J. Pathol. 201:204-212.
Muley, Ajit et al. (Mar. 2010) "Secreted Frizzled-Related Protein 4 An Angiogenesis Inhibitor"; The American Journal of Pathology, 176(3):1505-1516.
Zetter, Bruce, (May 1980) "Migration of capillary endothelial cells is stimulated by Tumour-derived factors", Nature 285:41-43.
Blood, C.H. and Zetter, B.R. (1990) "Tumor interactions with the vasaculature:angiogenesis and tumor metastasis" Biochemica et Biophysica Acta, 1032:89-118.
Pawelatz, N. and Knierim, M. (1989) "Tumor-related Angiogenesis" Critical Reviews in Oncology/Hematology 9(3):197-242.
D'Amore, P.A. and Thompson, R.W., (1987) "Mechanisms of Angiogenesis", Ann. Rev. Physiol. 49:453-64.

* cited by examiner

*Primary Examiner* — Christine J Saoud
*Assistant Examiner* — Jegatheesan Seharaseyon
(74) *Attorney, Agent, or Firm* — Kathleen Williams; Amy DeCloux; Edwards Wildman Palmer LLP

(57) ABSTRACT

The present invention relates to the use of sFRP-4 and functional variants thereof as anti-angiogenic agents. It relates to methods of treatment and screening methods using sFRP-4 and functional variants thereof. Further, it relates to compositions, and in particular pharmaceutical composition, including sFRP-4 and functional variants thereof which may be used in the various methods provided herein.

5 Claims, 21 Drawing Sheets

Figure 1A (SEQ ID NO: 1)

```
MFLSILVALC LWLHLALGVR GAPCEAVRIP MCRHMPWNIT RMPNHLHHST QENAILAIEQ    60
YEELVDVNCS AVLRFFLCAM YAPICTLEFL HDPIKPCKSV CQRARDDCEP LMKMYNHSWP   120
ESLACDELPV YDRGVCISPE AIVTDLPEDV KWIDITPDMM VQERPLDVDC KRLSPDRCKC   180
KKVKPTLATY LSKNYSYVIH AKIKAVQRSG CNEVTTVVDV KEIFKSSSPI PRTQVPLITN   240
SSCQCPHILP HQDVLIMCYE WRSRMMLLEN CLVEKWRDQL SKRSIQWEER LQEQRRTVQD   300
KKKTAGRTSR SNPPKPKGKP PAPKPASPKK NIKTRSAQKR TNPKRV                  346
```

Figure 1B (SEQ ID NO: 2)

```
GAPCEAVRIP MCRHMPWNIT RMPNHLHHST QENAILAIEQ YEELVDVNCS AVLRFFLCAM    60
YAPICTLEFL HDPIKPCKSV CQRARDDCEP LMKMYNHSWP ESLACDELPV YDRGVCISPE   120
AIVTDLPEDV KWIDITPDMM VQERPLDVDC KRLSPDRCKC KKVKPTLATY LSKNYSYVIH   180
AKIKAVQRSG CNEVTTVVDV KEIFKSSSPI PRTQVPLITN SSCQCPHILP HQDVLIMCYE   240
WRSRMMLLEN CLVEKWRDQL SKRSIQWEER LQEQRRTVQD KKKTAGRTSR SNPPKPKGKP   300
PAPKPASPKK NIKTRSAQKR TNPKRV                                        326
```

Wild type sFRP4 (SEQ ID NO: 1)

```
MFLSILVALC  LWLHLALGVR  GAPCEAVRIP  MCRHMPWNIT  RMPNHLHHST  QENAILAIEQ    60
YEELVDVNCS  AVLRFFLCAM  YAPICTLEFL  HDPIKPCKSV  CQRARDDCEP  LMKMYNHSWP   120
ESLACDELPV  YDRGVCISPE  AIVTDLPEDV  KWIDITPDMM  VQERPLDVDC  KRLSPDRCKC   180
KKVKPTLATY  LSKNYSYVIH  AKIKAVQRSG  CNEVTTVVDV  KEIFKSSSPI  PRTQVPLITN   240
SSCQCPHILP  HQDVLIMCYE  WRSRMMLLEN  CLVEKWRDQL  SKRSIQWEER  LQEQRRTVQD   300
KKKTAGRTSR  SNPPKPKGKP  PAPKPASPKK  NIKTRSAQKR  TNPKRV                   346
```

Linker Sequence (SEQ ID NO: 9)

```
WDPPVAT                                                                    7
```

N1 eGFP (SEQ ID NO: 10)

```
MVSKGEELFT  GVVPILVELD  GDVNGHKFSV  SGEGEGDATY  GKLTLKFICT  TGKLPVPWPT    60
LVTTLTYGVQ  CFSRYPDHMK  QHDFFKSAMP  EGYVQERTIF  FKDDGNYKTR  AEVKFEGDTL   120
VNRIELKGID  FKEDGNILGH  KLEYNYNSHN  VYIMADKQKN  GIKVNFKIRH  NIEDGSVQLA   180
DHYQQNTPIG  DGPVLLPDNH  YLSTQSALSK  DPNEKRDHMV  LLEFVTAAGI  TLGMDELYK    239
```

CRD fragment (SEQ ID NO: 11)

```
MFLSILVALC  LWLHLALGVR  GAPCEAVRIP  MCRHMPWNIT  RMPNHLHHST  QENAILAIEQ    60
YEELVDVNCS  AVLRFFLCAM  YAPICTLEFL  HDPIKPCKSV  CQRARDDCEP  LMKMYNHSWP   120
ESLACDELPV  YDRGVCISPE  AIVT                                             144
```

Netrin fragment (SEQ ID NO: 12)

```
MFLSILVALC  LWLHLALGVK  GAPCKCKKVK  PTLATYLSKN  YSYVIHAKIK  AVQRSGCNEV    60
TTVVDVKEIF  KSSSPIPRTQ  VPLITNSSCQ  CPHILPHQDV  LIMCYEWRSR  MMLLENCLVE   120
KWRDQLSKRS  IQWEERLQEQ  RRTVQDKKKT  AGRTSRSNPP  KPKGKPPAPK  PASPKKNIKT   180
RSAQKRTNPK  RV                                                           192
```

Figure 14

SEQUENCE LISTING

```
<160> NUMBER OF SEQ ID NOS: 12

<210> SEQ ID NO 1
<211> LENGTH: 346
<212> TYPE: PRT
<213> ORGANISM: Homo sapiens

<400> SEQUENCE: 1

Met Phe Leu Ser Ile Leu Val Ala Leu Cys Leu Trp Leu His Leu Ala
1               5                   10                  15

Leu Gly Val Arg Gly Ala Pro Cys Glu Ala Val Arg Ile Pro Met Cys
                20                  25                  30

Arg His Met Pro Trp Asn Ile Thr Arg Met Pro Asn His Leu His His
            35                  40                  45

Ser Thr Gln Glu Asn Ala Ile Leu Ala Ile Glu Gln Tyr Glu Glu Leu
        50                  55                  60

Val Asp Val Asn Cys Ser Ala Val Leu Arg Phe Phe Leu Cys Ala Met
65                  70                  75                  80

Tyr Ala Pro Ile Cys Thr Leu Glu Phe Leu His Asp Pro Ile Lys Pro
                85                  90                  95

Cys Lys Ser Val Cys Gln Arg Ala Arg Asp Asp Cys Glu Pro Leu Met
                100                 105                 110
```

```
Lys Met Tyr Asn His Ser Trp Pro Glu Ser Leu Ala Cys Asp Glu Leu
        115                 120                 125

Pro Val Tyr Asp Arg Gly Val Cys Ile Ser Pro Glu Ala Ile Val Thr
130                 135                 140

Asp Leu Pro Glu Asp Val Lys Trp Ile Asp Ile Thr Pro Asp Met Asn
145                 150                 155                 160

Val Gln Glu Arg Pro Leu Asp Val Asp Cys Lys Arg Leu Ser Pro Asp
                165                 170                 175

Arg Cys Lys Cys Lys Lys Val Lys Pro Thr Leu Ala Thr Tyr Leu Ser
                180                 185                 190

Lys Asn Tyr Ser Tyr Val Ile His Ala Lys Ile Lys Ala Val Gln Arg
            195                 200                 205

Ser Gly Cys Asn Glu Val Thr Thr Val Val Asp Val Lys Glu Ile Phe
        210                 215                 220

Lys Ser Ser Ser Pro Ile Pro Arg Thr Gln Val Pro Leu Ile Thr Asn
225                 230                 235                 240

Ser Ser Cys Gln Cys Pro His Ile Leu Pro His Gln Asp Val Leu Ile
                245                 250                 255

Met Cys Tyr Glu Trp Arg Ser Arg Met Met Leu Leu Glu Asn Cys Leu
                260                 265                 270

Val Glu Lys Trp Arg Asp Gln Leu Ser Lys Arg Ser Ile Gln Trp Glu
            275                 280                 285

Glu Arg Leu Gln Glu Gln Arg Arg Thr Val Gln Asp Lys Lys Lys Thr
        290                 295                 300

Ala Gly Arg Thr Ser Arg Ser Asn Pro Pro Lys Pro Lys Gly Lys Pro
305                 310                 315                 320

Pro Ala Pro Lys Pro Ala Ser Pro Lys Lys Asn Ile Lys Thr Arg Ser
                325                 330                 335

Ala Gln Lys Arg Thr Asn Pro Lys Arg Val
                340                 345

<210> SEQ ID NO 2
<211> LENGTH: 326
<212> TYPE: PRT
<213> ORGANISM: HOMO SAPIENS

<400> SEQUENCE: 2

Gly Ala Pro Cys Glu Ala Val Arg Ile Pro Met Cys Arg His Met Pro
1               5                   10                  15

Trp Asn Ile Thr Arg Met Pro Asn His Leu His His Ser Thr Gln Glu
            20                  25                  30

Asn Ala Ile Leu Ala Ile Glu Gln Tyr Glu Glu Leu Val Asp Val Asn
        35                  40                  45

Cys Ser Ala Val Leu Arg Phe Phe Leu Cys Ala Met Tyr Ala Pro Ile
    50                  55                  60

Cys Thr Leu Glu Phe Leu His Asp Pro Ile Lys Pro Cys Lys Ser Val
65                  70                  75                  80

Cys Gln Arg Ala Arg Asp Asp Cys Glu Pro Leu Met Lys Met Tyr Asn
                85                  90                  95

His Ser Trp Pro Glu Ser Leu Ala Cys Asp Glu Leu Pro Val Tyr Asp
            100                 105                 110

Arg Gly Val Cys Ile Ser Pro Glu Ala Ile Val Thr Asp Leu Pro Glu
        115                 120                 125

Asp Val Lys Trp Ile Asp Ile Thr Pro Asp Met Met Val Gln Glu Arg
130                 135                 140
```

```
Pro Leu Asp Val Asp Cys Lys Arg Leu Ser Pro Asp Arg Cys Lys Cys
145                 150                 155                 160

Lys Lys Val Lys Pro Thr Leu Ala Thr Tyr Leu Ser Lys Asn Tyr Ser
            165                 170                 175

Tyr Val Ile His Ala Lys Ile Lys Ala Val Gln Arg Ser Gly Cys Asn
            180                 185                 190

Glu Val Thr Thr Val Val Asp Val Lys Glu Ile Phe Lys Ser Ser Ser
        195                 200                 205

Pro Ile Pro Arg Thr Gln Val Pro Leu Ile Thr Asn Ser Ser Cys Gln
210                 215                 220

Cys Pro His Ile Leu Pro His Gln Asp Val Leu Ile Met Cys Tyr Glu
225                 230                 235                 240

Trp Arg Ser Arg Met Met Leu Leu Glu Asn Cys Leu Val Glu Lys Trp
                245                 250                 255

Arg Asp Gln Leu Ser Lys Arg Ser Ile Gln Trp Glu Arg Leu Gln
            260                 265                 270

Glu Gln Arg Arg Thr Val Gln Asp Lys Lys Thr Ala Gly Arg Thr
        275                 280                 285

Ser Arg Ser Asn Pro Pro Lys Pro Lys Gly Lys Pro Pro Ala Pro Lys
290                 295                 300

Pro Ala Ser Pro Lys Lys Asn Ile Lys Thr Arg Ser Ala Gln Lys Arg
305                 310                 315                 320

Thr Asn Pro Lys Arg Val
            325

<210> SEQ ID NO 3
<211> LENGTH: 20
<212> TYPE: DNA
<213> ORGANISM: ARTIFICIAL SEQUENCE
<220> FEATURE:
<223> OTHER INFORMATION: SENSE PRIMER FOR SFRP4

<400> SEQUENCE: 3
cacaggaaac agctatgacc                                         20

<210> SEQ ID NO 4
<211> LENGTH: 25
<212> TYPE: DNA
<213> ORGANISM: ARTIFICIAL SEQUENCE
<220> FEATURE:
<223> OTHER INFORMATION: ANTISENSE PRIMER FOR SFRP4

<400> SEQUENCE: 4
gctggatccc acactctttt cgggt                                   25

<210> SEQ ID NO 5
<211> LENGTH: 20
<212> TYPE: DNA
<213> ORGANISM: ARTIFICIAL SEQUENCE
<220> FEATURE:
<223> OTHER INFORMATION: SENSE PRIMER

<400> SEQUENCE: 5
cacaggaaac agctatgacc                                         20

<210> SEQ ID NO 6
<211> LENGTH: 25
<212> TYPE: DNA
<213> ORGANISM: ARTIFICIAL SEQUENCE
<220> FEATURE:
<223> OTHER INFORMATION: ANTISENSE PRIMER
```

-continued

<400> SEQUENCE: 6
atcctccggg ggatccgtga cgatg    25

<210> SEQ ID NO 7
<211> LENGTH: 33
<212> TYPE: DNA
<213> ORGANISM: ARTIFICIAL SEQUENCE
<220> FEATURE:
<223> OTHER INFORMATION: SENSE PRIMER CONTAINING AN ASCI SITE

<400> SEQUENCE: 7
gactgtaaag gcgcgccccc cgatcggtgc aag    33

<210> SEQ ID NO 8
<211> LENGTH: 25
<212> TYPE: DNA
<213> ORGANISM: ARTIFICIAL SEQUENCE
<220> FEATURE:
<223> OTHER INFORMATION: ANTI-SENSE PRIMER

<400> SEQUENCE: 8
gctggatccc acactctttt cgggt    25

<210> SEQ ID NO 9
<211> LENGTH: 7
<212> TYPE: PRT
<213> ORGANISM: ARTIFICIAL SEQUENCE
<220> FEATURE:
<223> OTHER INFORMATION: LINKER SEQUENCE

<400> SEQUENCE: 9

Trp Asp Pro Pro Val Ala Thr
1               5

<210> SEQ ID NO 10
<211> LENGTH: 239
<212> TYPE: PRT
<213> ORGANISM: ARTIFICIAL SEQUENCE
<220> FEATURE:
<223> OTHER INFORMATION: N1 EGFP

<400> SEQUENCE: 10

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

```
Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
                195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235

<210> SEQ ID NO 11
<211> LENGTH: 144
<212> TYPE: PRT
<213> ORGANISM: ARTIFICIAL SEQUENCE
<220> FEATURE:
<223> OTHER INFORMATION: CRD FRAGMENT

<400> SEQUENCE: 11

Met Phe Leu Ser Ile Leu Val Ala Leu Cys Leu Trp Leu His Leu Ala
1               5                   10                  15

Leu Gly Val Arg Gly Ala Pro Cys Glu Ala Val Arg Ile Pro Met Cys
            20                  25                  30

Arg His Met Pro Trp Asn Ile Thr Arg Met Pro Asn His Leu His His
        35                  40                  45

Ser Thr Gln Glu Asn Ala Ile Leu Ala Ile Glu Gln Tyr Glu Glu Leu
    50                  55                  60

Val Asp Val Asn Cys Ser Ala Val Leu Arg Phe Phe Leu Cys Ala Met
65                  70                  75                  80

Tyr Ala Pro Ile Cys Thr Leu Glu Phe Leu His Asp Pro Ile Lys Pro
                85                  90                  95

Cys Lys Ser Val Cys Gln Arg Ala Arg Asp Asp Cys Glu Pro Leu Met
            100                 105                 110

Lys Met Tyr Asn His Ser Trp Pro Glu Ser Leu Ala Cys Asp Glu Leu
        115                 120                 125

Pro Val Tyr Asp Arg Gly Val Cys Ile Ser Pro Glu Ala Ile Val Thr
    130                 135                 140

<210> SEQ ID NO 12
<211> LENGTH: 192
<212> TYPE: PRT
<213> ORGANISM: ARTIFICIAL SEQUENCE
<220> FEATURE:
<223> OTHER INFORMATION: NETRIN FRAGMENT

<400> SEQUENCE: 12

Met Phe Leu Ser Ile Leu Val Ala Leu Cys Leu Trp Leu His Leu Ala
1               5                   10                  15

Leu Gly Val Arg Gly Ala Pro Cys Lys Cys Lys Val Lys Pro Thr
            20                  25                  30

Leu Ala Thr Tyr Leu Ser Lys Asn Tyr Ser Tyr Val Ile His Ala Lys
        35                  40                  45

Ile Lys Ala Val Gln Arg Ser Gly Cys Asn Glu Val Thr Thr Val Val
    50                  55                  60

Asp Val Lys Glu Ile Phe Lys Ser Ser Pro Ile Pro Arg Thr Gln
65                  70                  75                  80

Val Pro Leu Ile Thr Asn Ser Ser Cys Gln Cys Pro His Ile Leu Pro
                85                  90                  95
```

-continued

```
His Gln Asp Val Leu Ile Met Cys Tyr Glu Trp Arg Ser Arg Met Met
            100                 105                 110

Leu Leu Glu Asn Cys Leu Val Glu Lys Trp Arg Asp Gln Leu Ser Lys
        115                 120                 125

Arg Ser Ile Gln Trp Glu Glu Arg Leu Gln Glu Gln Arg Arg Thr Val
        130                 135                 140

Gln Asp Lys Lys Thr Ala Gly Arg Thr Ser Arg Ser Asn Pro Pro
145                 150                 155                 160

Lys Pro Lys Gly Lys Pro Pro Ala Pro Lys Pro Ala Ser Pro Lys Lys
            165                 170                 175

Asn Ile Lys Thr Arg Ser Ala Gln Lys Arg Thr Asn Pro Lys Arg Val
            180                 185                 190
```

ANTI-ANGIOGENIC AGENTS AND METHODS OF THEIR USE

RELATED APPLICATIONS

This is a continuation utility patent application which claims priority to International Application No: PCT/AU2007/000477, filed on Apr. 11, 2007, which claims priority to Australian Patent Application No. 2006901898, filed on Apr. 11, 2008.

Both applications are herein incorporated by reference in their entirety.

FIELD OF THE INVENTION

The present invention relates to the use of sFRP-4 and functional variants thereof as antiangiogenic agents. It relates to methods of treatment and screening methods using sFRP-4 and functional variants thereof. Further, it relates to compositions, and in particular pharmaceutical composition, including sFRP-4 and functional variants thereof which may be used in the various methods provided herein.

BACKGROUND

Angiogenesis occurs in the healthy body for healing wounds and for restoring blood flow to tissues after injury or insult. In females, angiogenesis also occurs during the monthly reproductive cycle (to rebuild the uterus lining, to mature the egg during ovulation) and during pregnancy (to build the placenta, the circulation between mother and fetus).

The healthy body controls angiogenesis through a series of "on" and "off" switches—angiogenesis stimulating factors and angiogenesis inhibitors or antiangiogenesis agents.

When angiogenic growth factors are produced locally in excess of angiogenesis inhibitors, the balance is tipped in favour of blood vessel growth. When inhibitors are present in excess of stimulators, angiogenesis is stopped. The normal, healthy body maintains a perfect balance of angiogenesis modulators. In general, angiogenesis is "turned off" by the production of more inhibitors than stimulators.

Improper maintenance of angiogenesis can manifest itself in a range of diseases and disorders. Whilst a number of angiogenesis modulators are known and have been characterised, to date, there is no effective therapy for a number of these diseases/disorders.

The present invention seeks to overcome or at least partially alleviate the above problems by identifying a new anti-angiogenic agent.

General

Those skilled in the art will appreciate that the invention described herein is susceptible to variations and modifications other than those specifically described. The invention includes all such variation and modifications. The invention also includes all of the steps, features, pharmaceutical compositions and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, pharmaceutical compositions and methods are clearly within the scope of the invention as described herein.

The invention described herein may include one or more range of values (eg. size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

SUMMARY OF THE INVENTION

Applicants have identified a new property of sFRP-4; its use as an antiangiogenic agent. Thus, the present invention provides for the use of sFRP-4 or a functional variant thereof for controlling angiogenesis. In particular it relates to a method for controlling angiogenesis, comprising the step of: applying sFRP-4 or a functional variant thereof to the angiogenesis.

The present invention also provides agonists, antagonists and methods of screening compounds to identify those that enhance or block the binding of sFRP-4 or functional variants thereof. Thus, the present invention also provides a screening method comprising the steps of: (i) detecting the presence and/or measuring the level sFRP-4 in a subject or a subject sample; and (ii) comparing the result from (i) with a reference measure indicative of normality.

The present invention also provides a method for treating a disease or disorder associated with undesirable levels of angiogenesis comprising the step of: administering to a subject an effective amount of sFRP-4 or a functional equivalent thereof.

The present invention provides for the prophylactic use of sFRP-4 or a functional variant thereof to reduce or prevent angiogenesis such as that caused by a disease or disorder. In particular it relates to a method for prophylactic treating a subject against undesirable levels of angiogenesis comprising the step of: administering to the subject an effective amount of sFRP-4 or a functional equivalent thereof.

This invention also provides pharmaceutical or veterinary compositions comprising sFRP-4 or a functional variant thereof and a pharmaceutically acceptable carrier.

The present invention also provides for the use of sFRP-4 or a functional variant thereof in the preparation of a medicament for treating or preventing a disease or disorder characterized by undesirable angiogenesis.

The present invention still further provides a method of identifying an endothelial cell sFRP-4 receptor comprising the steps of: (i) contacting an endothelial cell or extract thereof with sFRP-4; (ii) isolating any complexes including sFRP-4 and a receptor; and (iii) characterising the receptor.

Other aspects and advantages of the invention will become apparent to those skilled in the art from a review of the ensuing description, which proceeds with reference to the following illustrative drawings.

BRIEF DESCRIPTION OF THE FIGURES

FIG. 1A is the amino acid sequence of sFRP-4.

FIG. 1B is the amino acid sequence of sFRP-4 minus the signal sequence.

FIG. 11A—Images from cotton plug assays showed a clear inhibition of blood vessel formation under Ang001 treatment. FIG. 11B—Hemoglobin measurement graph showed less hemoglobin content following sFRP-4 treatment. (n=5) *Significantly different from control sets. ($p<0.05$)

FIG. 12A—Images from spongemat assays showed a clear inhibition in blood vessel formation under sFRP-4 treatment. FIG. 12B—Hemoglobin measurement graph showed less hemoglobin content under sFRP-4 treatment. (n=3) *Significantly different from control sets. ($p<0.05$)

FIG. 14—provides sequences of various FRP-4 fragments.

DETAILED DESCRIPTION OF THE INVENTION

Figure 2A:
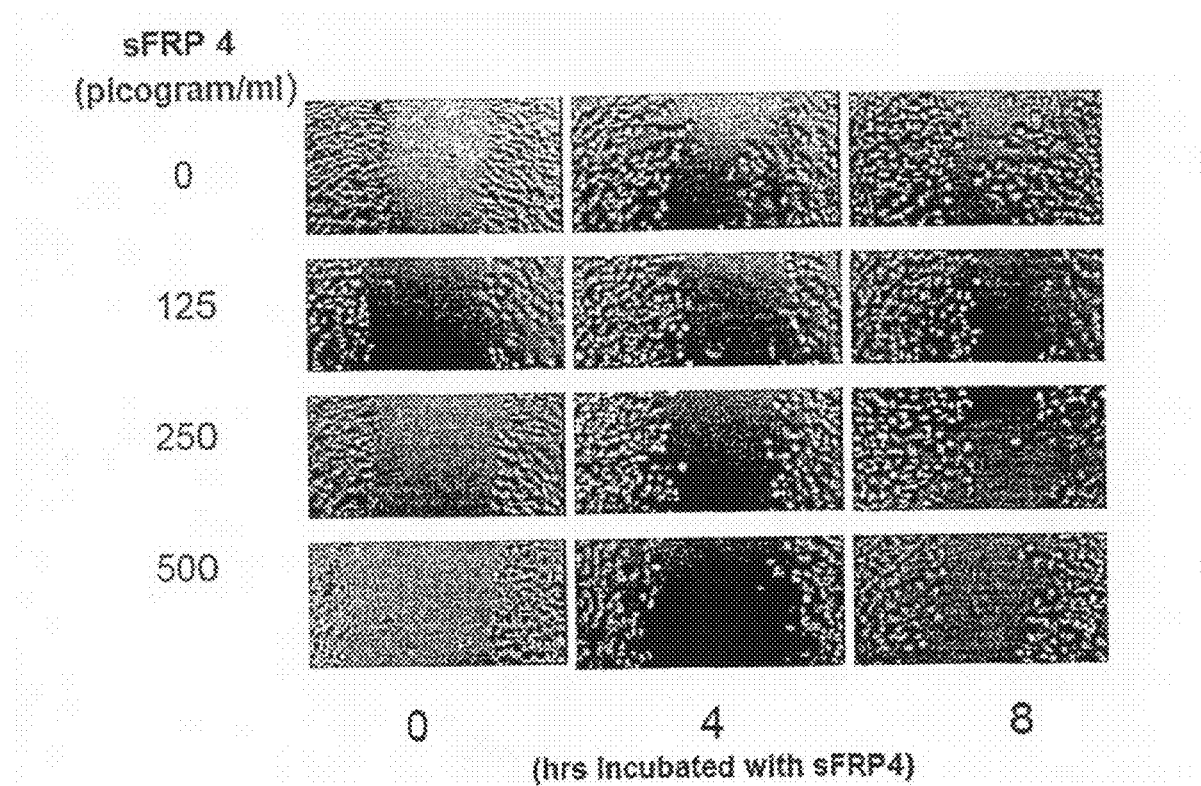
FIG. 2A—Microscopy images showing the results of the wound healing assay (4× and 40× magnification) with different concentrations of sFRP-4. Wound healing assays showed slower movement of cells under sFRP-4 treatment. In both 4× and 40× images it was very clear that sFRP-4 stops migration of the cells.

Consistent with the revelations made by the inventors, the present invention provides for the use of sFRP-4 or a functional variant thereof for modulating angiogenesis.

Thus, in one form the present invention resides in a method for controlling or modulating angiogenic activity, said method comprising the step of: contacting angiogenic tissue with an anti-angiogenic amount of sFRP-4 or a functional variant thereof.

Alternatively, the invention resides in the use of an anti-angiogenic amount of sFRP-4 or a functional variant thereof in the manufacture of a medicament for the treatment of angiogenic activity.

As used herein "angiogenesis" is used to summarise a myriad of different cellular events that occur after vasculogenesis that lead to the development of new blood vessels through sprouting from pre-existing vessels. This process involves the migration and proliferation of endothelial cells from pre-existing vessels. Angiogenesis is not limited to the embryonic period of development but also occurs in adults where the formation of vessels is required and is of particular significance in wound healing, maturation of ovarian follicles and tumour development.

Whilst the applicant does not wish to be bound by any particular mode of action it is believed that sFRP-4 exerts its angiogenesis related activity via endothelial cell receptor signalling.

The full amino acid sequence of sFRP-4 is provided herein as FIG. 1A (SEQ ID NO: 1). In FIG. 1A amino acids 19-139 represent the cysteine rich (FZ) domain (CRD), amino acids 23-140 represent the frizzled domain, amino acids 187-290 represent the netrin like domain or netrin C terminal like domain (NLD), amino acids 291-346 represent a hydrophilic region and the signal sequence is represented by amino acids 1 to 18. Disulphide bonds are located at amino acids 24-85, 32-78, 69-108, 97-136 and 101-125 and there are glycosylation sites at amino acids 38 and 194. FIG. 1B represents the amino acid sequence of sFRP-4 minus the signal sequence (SEQ ID NO: 2).

For the purposes of the present invention the term "sFRP-4" is a protein comprising SEQ ID NO: 1 or SEQ ID NO: 2. Furthermore, "functional variants" of the present invention include peptides and non-peptide mimetics that retain at least one important characteristic of SEQ ID NO: 1 or 2 such as its antiangiogenic activity. Examples of functional variants of the present invention are peptides that comprise the CRD and/or the NLD region of SEQ ID NO: 1 or 2.

The peptides may be recombinant, natural or synthetic. Methods for screening for functional variants including agonists are described in more detail hereunder.

Thus, functional variants of the invention also include variants of sFRP-4 with deletions, insertions, inversions, repeats, and type substitutions. Guidance concerning which amino acid changes are likely to be phenotypically silent can be found in Bowie, J. U., et al, "Deciphering the Message in Protein Sequences: Tolerance to Amino Acid Substitutions," *Science* 247:1306-1310 (1990).

A functional variant of sFRP-4 may be: (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which sFRP-4 is fused with another compound, such as a compound to increase its half life (for example, polyethylene glycol or polypropylene glycol), or (iv) one in which the additional amino acids are fused to sFRP-4, such as a leader or secretory sequence or a sequence which is employed for purification or a proprotein sequence. Such fragments, derivatives and analogs are deemed to be within the scope of functional variants for the purposes of the present invention.

Of particular interest is the replacement of amino acids that alter the antiangiogenesis activity or binding affinity of sFRP-4. Thus, the functional variants of the present invention may include one or more amino acid substitutions, deletions or additions, relative to SEQ ID NO: 1 or 2, either from natural mutations or human manipulation. The particular replacements may be determined by a skilled person as detailed more fully hereunder. However, changes are preferably of a minor nature, such as conservative amino acid substitutions that do not significantly affect the folding or activity of the protein (see for example the table hereunder). Amino acids in the same block in the second column and preferably in the same line in the third column may be substituted for each other

| ALIPHATIC | Non-polar | G A P |
|  |  | I L V |
|  | Polar-uncharged | C S T M |
|  |  | N Q |
|  | Polar-charged | D E |
|  |  | K R |
| AROMATIC |  | H F W Y |

Amino acids that are essential for function, such as antiangiogenesis and or receptor binding, can be identified by methods known in the art, such as site directed mutagenesis or alanine-scanning mutagenesis. The latter procedure introduces single alanine mutations at every residue in the molecule. The resulting mutant molecules are then tested for biological activity such as antiangiogenesis. Sites that are critical for ligand-receptor binding can also be determined by structural analysis such as crystallization. Nuclear magnetic resonance or photoaffinity labelling may also be used when developing functional variants. Alternatively, synthetic peptides corresponding to candidate functional variants may be produced and their ability to display antiangiogenesis properties in vitro or in vivo assessed.

Functional variants can be prepared as libraries having sequences based on SEQ ID NO: 1 or 2, but with various changes. Phage display can also be effective in identifying functional variants with useful properties. Briefly, one prepares a phage library (using e.g. M13, fd, or lambda phage), displaying inserts from 4 to about 20, 40 or 80 amino acid residues using conventional procedures. The inserts may represent, for example, a biased degenerate array or may completely restrict the amino acids at one or more positions. One can then select phage-bearing inserts that have a relevant biological activity such as antiangiogenesis or receptor binding. This process can be repeated through several cycles of reselection of phage. Repeated rounds lead to enrichment of phages bearing particular sequences. DNA sequence analysis can be conducted to identify the sequences of the expressed polypeptides. The minimal linear portion of a sequence that confers the relevant activity can be determined. One can repeat the procedure using a biased library containing inserts containing part or the entire minimal linear portion plus one or more additional degenerate residues upstream or downstream thereof.

Functional variants can be tested for retention of any of the useful properties of sFRP-4. For example, they can be tested for in vitro properties, initially on endothelial cells, to determine which ones retain particular activities. These in vitro properties include the ability of a functional variant to inhibit wound healing, tube formation, migration, membrane permeability, nitric oxide (NO) production and/or blood vessel formation in endothelial cell culture. Peptides that retain or lack a relevant property can then be used in in vivo assays.

In vitro angiogenic assays include, for example, Proliferation assays, Three Dimensional Gel assay (eg Type I Collagen gel assays, Matrigel assays, and Fibrin gel assays), Wound type assays, Permeability assay and Aortic Ring model assays. In vivo angiogenic assays include, for example, Chicken Chorioallantoic Membrane assays, Corneal Neovascularisation assay, and Pouch assays. The method for performance of these assays may be found in a wide range of text and articles that flood the field, however, as a general guide these assays are discussed in more details in Cockerill, Gamble, Vadas (1994) "Angiogenesis: models and model vectors". In: International Reviews of Cytology. A Survey of Cell Biology 159: 113-160, and Litwin, Gamble, Vadas, 1995, "Role of growth factors in endothelial cell functions." In: Human Growth factors: Their role in Disease and Therapy, B B Aggarwal & R K Puri (Eds), Blackwell Science, Inc. USA Chapter 7 101-129, each of which is expressly incorporated herein by reference.

Preferred functional variants of the present invention comprise an amino acid sequence that is at least 50-80% identical, more preferably at least 85%, 90% or 95% identical, still more preferably at least 96%, 97%, 98% or 99% identical to SEQ ID NO: 1 or 2.

By a polypeptide having an amino acid sequence at least, for example, 95% "identical" to a reference amino acid sequence it is intended that the amino acid sequence of the polypeptide is identical to the reference sequence except that the polypeptide sequence may include up to five amino acid alterations per each 100 amino acids of the reference polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to a reference sequence can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence, the parameters are set, of course, such that the percentage of identity is calculated over the full length of the reference amino acid sequence and that gaps in homology of up to 5% of the total number of amino acid residues in the reference sequence are allowed.

In general, the functional variants of the present invention can be synthesized directly or obtained by chemical or mechanical disruption of larger molecules, fractioned and then tested for one or more activity of the native molecule such as antiangiogenic activity. Functional variants with useful properties may also be obtained by mutagenesis of a specific region of the nucleotide encoding the polypeptide, followed by expression and testing of the expression product, such as by subjecting the expression product to in vitro tests on endothelial cells to assess antiangiogenesis activity and/or receptor binding. Functional variants may also be produced by Northern blot analysis of total cellular RNA followed by cloning and sequencing of identified bands derived from different tissues/cells, or by PCR analysis of such RNA also followed by cloning and sequencing. Thus, synthesis or purification of an extremely large number of functional variants is possible using the information contained herein.

Functional variants also include conformationally constrained peptides. Conformational constraint refers to the stability and preferred conformation of the three-dimensional shape assumed by a peptide. Conformational constraints include local constraints, involving restricting the conformational mobility of a single residue in a peptide; regional constraints, involving restricting the conformational mobility of a group of residues, which residues may form some secondary structural unit; and global constraints, involving the entire peptide structure.

The active conformation of a peptide may be stabilized by a covalent modification, such as cyclization or by incorporation of gamma-lactam or other types of bridges. For example, side chains can be cyclized to the backbone to create an L-gamma-lactam moiety on each side of the interaction site. Cyclization also can be achieved, for example, by formation of cysteine bridges, coupling of amino and carboxy terminal groups of respective terminal amino acids, or coupling of the amino group of a Lys residue or a related homolog with a carboxy group of Asp, Glu or a related homolog. Coupling of the alpha-amino group of a polypeptide with the epsilon-amino group of a lysine residue, using iodoacetic anhydride, can be also undertaken.

Another approach is to include a metal-ion complexing backbone in the peptide structure. Typically, the preferred metal-peptide backbone is based on the requisite number of particular coordinating groups required by the coordination sphere of a given complexing metal ion. In general, most of the metal ions that may prove useful have a coordination number of four to six. The nature of the coordinating groups in the peptide chain includes nitrogen atoms with amine, amide, imidazole, or guanidino functionalities; sulphur atoms of thiols or disulfides; and oxygen atoms of hydroxy, phenolic, carbonyl, or carboxyl functionalities. In addition, the peptide chain or individual amino acids can be chemically altered to include a coordinating group, such as for example oxime, hydrazino, sulfhydryl, phosphate, cyano, pyridino, piperidino, or morpholino. The peptide construct can be either linear or cyclic. However a linear construct is typically preferred. One example of a small linear peptide is Gly-Gly-Gly-Gly that has four nitrogens (an $N_4$ complexation system) in the backbone that can complex to a metal ion with a coordination number of four.

Functional variants of the present invention may also be determined by relying upon the development of amino acid sequence motifs to which potential epitopes may be compared. Each motif describes a finite set of amino acid sequences in which the residues at each (relative) position may be (a) restricted to a single residue, (b) allowed to vary amongst a restricted set of residues, or (c) allowed to vary amongst all possible residues. For example, a motif might specify that the residue at a first position may be any one of valine, leucine, isoleucine, methionine, or phenylalanine; that the residue at the second position must be histidine; that the residue at the third position may be any amino acid residue; that the residue at the fourth position may be any one of the residues valine, leucine, isoleucine, methionine, phenylalanine, tyrosine or tryptophan; that the residue at the fifth position must be lysine, and so on.

Sequence motifs for SEQ ID NO: 1 or 2 can be developed further by analysis of protein structure and conformation. By providing a detailed structural analysis of the residues involved in forming the contact surfaces of the peptide, one is enabled to make predictions of sequence motifs that have similar binding properties.

Using these sequence motifs as search, evaluation, or design criteria, one is enabled to identify classes of peptides that represent functional variants that have a reasonable likelihood of binding to the target and inducing a desired biological effect. These peptides can be synthesized and tested for activity as described herein. Use of these motifs, as opposed to pure sequence homology or sequence homology with unlimited "conservative" substitutions, represents a method by which one of ordinary skill in the art can further evaluate peptides for potential application in the treatment of diseases associated with angiogenesis.

Thus, the present invention also provides methods for identifying functional variants of sFRP-4. In general, a first amino acid residue of SEQ ID NO: 1 or 2 is mutated to prepare a variant peptide. In one embodiment, the amino acid residue can be selected and mutated as indicated by a computer model of peptide conformation. Peptides bearing mutated residues that maintain a similar conformation (e.g. secondary structure) can be considered potential functional variants that can be tested for function using the assays described herein. Any method for preparing variant peptides can be employed, such as synthesis of the variant peptide, recombinantly producing the variant peptide using a mutated nucleic acid molecule, and the like. The properties of the variant peptide in relation to the native sequence are then determined according to standard procedures as described herein.

Functional variants prepared by any of the foregoing methods can be sequenced, if necessary, to determine the amino acid sequence and thus deduce the nucleotide sequence which encodes such variants.

The functional variants of sFRP-4 also extend to fragments. Preferably, the fragments retain anti-angiogenesis activity, such as an ability to inhibit wound healing, tube formation, migration, membrane permeability, NO production and/or blood vessel formation in endothelial cells, or may be made intentionally to reduce or remove a biological activity of the polypeptide.

Other polypeptide fragments of the present invention are those that comprise a sequence based on SEQ ID NO: 1 or 2 but lack a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Again, these truncation mutants preferably retain at least one biological activity of the full polypeptide.

Preferably, the fragments of the present invention comprise at least 10, 20, 30, 50 or 100 amino acid residues. Preferably, the fragments include at least one biological activity of sFRP-4, such as antiangiogenesis and/or ability to bind a receptor for the full molecule or an antibody thereto.

Fragments or portions of the polypeptides of the present invention may be employed for producing the corresponding full-length polypeptide by peptide synthesis; therefore, the fragments may be employed as intermediates for producing the full-length polypeptides.

Representative examples of polypeptide fragments of the invention include those which are about 5-15, 10-20, 15-40, 30-55, 41-75, 41-80, 41-90; 50-100, 75-100, 90-115, 100-125 and 110-130 amino acids in length. In this context "about" includes the particularly recited range and ranges larger or smaller by several, a few, 5, 4, 3, 2 or 1 amino acid residues at either extreme or at both extremes. For instance, about 40-90 amino acids in this context means a polypeptide fragment of 40 plus or minus several, a few, 5, 4, 3, 2 or 1 amino acid residues to 90 plus or minus several a few, 5, 4, 3, 2 or 1 amino acid residues, i.e., ranges as broad as 40 minus several amino acids to 90 plus several amino acids to as narrow as 40 plus several amino acids to 90 minus several amino acids. Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes of the recited ranges with no additions or deletions. Most highly preferred of all in this regard are fragments from 5-15, 10-20, 15-40, 30-55, 41-75, 41-80, 41-90, 50-100, 75-100, 90-115, 100-125, and 110-130 amino acids long.

Other fragments of the present invention comprise an epitope-bearing portion of sFRP-4. Preferably, the epitope is an immunogenic or antigenic epitope of the polypeptide. An "immunogenic epitope" is defined as a part of a protein that elicits an antibody response when the whole protein is the immunogen. On the other hand, a region of a protein molecule to which an antibody can bind is defined as an "antigenic epitope."

As to the selection of fragments bearing an antigenic epitope (i.e., that contain a region of a protein to which an antibody can bind), it is well known in that art that relatively short synthetic peptides that mimic part of a protein sequence are routinely capable of eliciting an antiserum that reacts with the partially mimicked protein. Peptides capable of eliciting protein-reactive sera are frequently represented in the primary sequence Z-1 of a protein, can be characterized by a set of simple chemical rules, and are confined neither to immunodominant regions of intact proteins (i.e. immunogenic epitopes) nor to the amino or carboxyl terminals. Antigenic epitope-bearing fragments of the invention are therefore useful to raise antibodies, including monoclonal antibodies that bind specifically to sFRP-4.

Antigenic epitope-bearing fragments preferably contain a sequence of at least 7, 9, 10 or at least about 15 to about 30 amino acids contained within the amino acid sequence of SEQ ID NO: 1 or 2 and may be contiguous or conformational epitopes. The epitope-bearing fragments the invention may be produced by any conventional means apparent to those skilled in the art.

Functional variants for the purposes of the present invention also include mimetics. Nonpeptide analogs of sFRP-4, e.g., those that provide a stabilized structure or lessened biodegradation, are contemplated. Peptide mimetic analogs can be prepared based on a selected peptide by replacement of one or more residues by nonpeptide moieties. Preferably, the nonpeptide moieties permit the peptide to retain its natural conformation, or stabilize a preferred, e.g., bioactive, conformation.

A wide variety of useful techniques may be used to elucidate the precise structure of a peptide. These techniques include amino acid sequencing, x-ray crystallography, mass spectroscopy, nuclear magnetic resonance spectroscopy, computer-assisted molecular modelling, peptide mapping, and combinations thereof. Structural analysis of a peptide generally provides a large body of data that comprise the amino acid sequence of the peptide as well as the three-dimensional positioning of its atomic components. From this information, non-peptide peptidomimetics may be designed that have the required chemical functionalities for therapeutic activity but are more stable, for example less susceptible to biological degradation.

sFRP-4 and functional variants thereof may also be provided conjugated to another molecule that confers another advantageous property. Fusion proteins where another peptide sequence is fused to sFRP-4, to aid in extraction and purification, is one example. Examples of fusion protein partners include glutathione-S-transferase (GST), hexahistidine, GAL4 (DNA binding and/or transcriptional activation domains) and β-galactosidase.

It may also be convenient to include a proteolytic cleavage site between the fusion protein partner and sFRP-4 or functional variant thereof to allow removal of fusion protein sequences. Preferably, the fusion protein will not hinder an important activity of the protein such as antiangiogenesis and/or receptor binding. Fusion proteins including a peptide adapted to target sFRP-4 or the functional equivalent to a cell type or tissue are another example.

sFRP-4 and functional variants thereof can also be conjugated to a moiety such as a fluorescent, radioactive, or enzymatic label (e.g. a detectable moiety, such as green fluorescent protein) or a molecule that enhances stability under assay conditions.

sFRP-4 and functional variants thereof can be conjugated to other compounds by well-known methods, including bifunctional linkers, formation of a fusion polypeptide, and formation of biotin/streptavidin or biotin/avidin complexes by attaching either biotin or streptavidin/avidin to the peptide or the complementary molecule. Depending upon the nature of the reactive groups in an isolated peptide and a targeting agent, a conjugate can be formed by simultaneously or sequentially allowing the functional groups of the above-described components to react with one another. For example, the targeting agent can be prepared with a sulfhydryl group at, e.g., the carboxyl terminus, which then is coupled to a derivatizing agent to form a carrier molecule. Next, the carrier molecule is attached via its sulfhydryl group, to the peptide. Many other possible linkages are known to those of skill in the art.

Conjugates of sFRP-4 or a functional variant thereof and a targeting agent are formed by allowing the functional groups of the agent or compound and the peptide to form a linkage, preferably covalent, using coupling chemistries known to those of ordinary skill in the art. Numerous art-recognized methods for forming a covalent linkage can be used. See, for example, March, J., Advanced-Organic Chemistry, 4th Ed., New York, N.Y., Wiley and Sons, 1985), pp. 326-1120.

In the event that sFRP-4 or the functional variants described herein exhibit reduced activity in a conjugated form, the covalent bond between the agents can be selected to be sufficiently labile (e.g., to enzymatic cleavage by an enzyme present in the target tissue) so that it is easily cleaved thereby releasing the free peptide. Biologically labile covalent linkages, e.g., imino bonds, and "active" esters can be used to form prodrugs where the covalently coupled peptide is found to exhibit reduced activity in comparison to the activity of the peptide alone.

It is envisioned that sFRP-4 and the functional variants described herein can be delivered to endothelial cells by site-specific means. Cell-type-specific delivery can be provided by conjugating a peptide to a targeting molecule, e.g., one that selectively binds to a target endothelial cell. One example of a well-known targeting vehicle is liposomes. Liposomes are commercially available from Gibco BRL (Gaithersburg, Md.). Numerous methods are published for making targeted liposomes. Liposome delivery can be provided by encapsulating an isolated polypeptide of the present invention in liposomes that include a cell-type-specific targeting molecule. Methods for targeted delivery of compounds to particular cell types are well-known to those of skill in the art.

In the absence of a free amino- or carboxyl-terminal functional group that can participate in a coupling reaction, such a group can be introduced, e.g., by introducing a cysteine (containing a reactive thiol group) into the peptide by synthesis or site directed mutagenesis. Disulfide linkages can be formed between thiol groups in, for example, the peptide and a targeting molecule. Alternatively, covalent linkages can be formed using bifunctional crosslinking agents, such as bis-maleimidohexane (which contains thiol-reactive maleimide groups and which forms covalent bonds with free thiols). See also the Pierce Co. Immunotechnology Catalogue and Handbook Vol. 1 for a list of exemplary homo- and hetero-bifunctional crosslinking agents, thiol-containing amines and other molecules with reactive groups.

In general, the conjugated peptides of the invention can be prepared by using well-known methods for forming amide, ester or imino bonds between acid, aldehyde, hydroxy, amino, or hydrazo groups on the respective conjugated peptide components. As would be apparent to one of ordinary skill in the art, reactive functional groups that are present in the amino acid side chains of the peptide preferably are protected, to minimize unwanted side reactions prior to coupling the peptide to the derivatizing agent and/or to the extracellular agent. As used herein, "protecting group" refers to a molecule which is bound to a functional group and which may be selectively removed therefrom to expose the functional group in a reactive form. Preferably, the protecting groups are reversibly attached to the functional groups and can be removed therefrom using, for example, chemical or other cleavage methods. Thus, for example, the peptides of the invention can be synthesized using commercially available side-chain-blocked amino acids (e.g., FMOC-derivatised amino acids from Advanced Chemtech Inc., Louisville, Ky.). Alternatively, the peptide side chains can be reacted with protecting groups after peptide synthesis, but prior to the covalent coupling reaction. In this manner, corrugated peptides of the invention can be prepared in which the amino acid side chains do not participate to any significant extent in the coupling reaction of the peptide to the cell-type-specific targeting agent.

It will be appreciated that the amino acids in the peptides of the present invention that are required for antiangiogenesis activity and/or receptor binding may be incorporated into larger peptides and still maintain their function. Preferably, the amino acids required for antiangiogenic activity are a contiguous sequence of between about 5 and 20 amino acids and more preferably between about 6 and 15 amino acids.

Preferably, the sFRP-4 or a functional variant thereof is non-hydrolyzable in that the bonds linking the amino acids of the peptide are less readily hydrolyzed than peptide bonds formed between L-amino acids. To provide such peptides, one may select isolated peptides from a library of non-hydrolyzable peptides, such as peptides containing one or more D-amino acids or peptides containing one or more non-hydrolyzable peptide bonds linking amino acids.

Alternatively, one can select peptides that are optimal for a preferred function (e.g. antiangiogenic effects) in assay systems described in the Examples and then modify such peptides as necessary to reduce the potential for hydrolysis by proteases. For example, to determine the susceptibility to proteolytic cleavage, peptides may be labelled and incubated with cell extracts or purified proteases and then isolated to determine which peptide bonds are susceptible to proteolysis, e.g., by sequencing peptides and proteolytic fragments. Alternatively, potentially susceptible peptide bonds can be identified by comparing the amino acid sequence of an isolated peptide with the known cleavage site specificity of a panel of proteases. Based on the results of such assays, individual peptide bonds that are susceptible to proteolysis can be replaced with non-hydrolyzable peptide bonds by in vitro synthesis of the peptide.

Many non-hydrolyzable peptide bonds are known in the art, along with procedures for synthesis of peptides containing such bonds. Non-hydrolyzable bonds include -psi[CH.sub.2 NH]-reduced amide peptide bonds, -psi[COCH.sub.2]-ketomethylene peptide bonds, -psi[CH(CN)NH]-(cyanomethylene)amino peptide bonds, -psi[CH.sub.2 CH(OH)]-hydroxyethylene peptide bonds, -psi[CH.sub.2 O]-peptide bonds, and -psi[CH.sub.2 S]-thiomethylene peptide bonds.

Likewise, various changes may be made including the addition of various side groups that do not affect the manner in which the peptide functions, or which favourably affect the manner in which the peptide functions. Such changes may involve adding or subtracting charge groups, substituting amino acids, adding lipophilic moieties that do not affect binding but that affect the overall charge characteristics of the molecule facilitating delivery across the blood-brain barrier, etc. For each such change, no more than routine experimentation is required to test whether the molecule functions according to the invention. One simply makes the desired change or selects the desired peptide and applies it in a fashion as described in detail in the examples.

One approach is to link the sFRP-4 or functional variant thereof to a variety of polymers, such as polyethylene glycol (PEG) and polypropylene glycol (PPG). Replacement of naturally occurring amino acids with a variety of uncoded or modified amino acids such as D-amino acids and N-methyl amino acids may also be used to modify peptides. Another approach is to use bifunctional crosslinkers, such as N-succinimidyl 3-(2 pyridyldithio)propionate, succinimidyl 6-[3-(2 pyridyldithio)propionamido]hexanoate, and sulfosuccinimidyl 6-[3-(2 pyridyldithio)propionamido]hexanoate.

Screening Methods, Agonists and Antagonists

The present invention also provides agonists, antagonists and methods of screening compounds to identify those that enhance or block the binding of sFRP-4 or functional variants thereof.

For example, a preparation containing endothelial cells may be contacted with a labelled sFRP-4 in the absence or the presence of a candidate molecule that may be an agonist or antagonist. The ability of the candidate molecule to bind the receptor itself is reflected in decreased binding of the labelled protein. Molecules that bind gratuitously, i.e., without inhibiting angiogenesis, are most likely to be good antagonists. Molecules that bind and inhibit angiogenesis are likely to be good agonists.

Another example of an assay for antagonists is a competitive assay that combines a sFRP-4 and a potential antagonist with endothelial cells under appropriate conditions for a competitive inhibition assay. The peptide can be labelled, such as by radioactivity, such that its binding to the endothelial cell can be determined accurately to assess the effectiveness of the potential antagonist.

Potential antagonists include small organic molecules, peptides, polypeptides and antibodies that bind to endothelial cells at the same site as sFRP-4 and thus prevent them binding, and the biological effects they confer. Potential antagonists also may be small organic molecules, a peptide, a polypeptide such as a closely related protein or antibody that binds to an alternative site on the endothelial cell and prevents the action of sFRP-4 by excluding polypeptide binding.

Given the role of sFRP-4 in angiogenesis, it may also be possible to screen patients who may be predisposed to poor outcomes from conditions characterized by undesirable angiogenesis such as: cancer e.g. breast, prostate, brain, pancreas, lung, stomach, ovary, and cervix; leukemia, oesophagus, skin, colorectal, bladder and lymphoma, diabetic blindness, age related macular degeneration, rheumatoid arthritis, psoriasis, glaucoma, retinitis pigmentosa, obesity, synovitis, osteomyelitis, endometriosis, ovarian cysts, inflammatory bowel and periodontal disease, ascites, peritoneal adhesions, primary pulmonary hypertension, nasal polyps, asthma, warts, allergic dermatitis, Karposi sarcoma, vascular malformations, DiGeorge Syndrome, atherosclerosis and reproductive disorders such as those associated with undesirable implantation and/or fertilization.

Thus, the present invention also provides a screening method comprising the steps of: (i) detecting the presence and/or measuring the level sFRP-4 in a patient or a patient sample; and (ii) comparing the result from (i) with a reference measure indicative of normality.

Methods of Treating Angiogenesis Related Disorders

There are many disorders associated with undesirable angiogenesis and the activity of sFRP-4 and functional equivalents thereof render them useful as treatment options. Thus, the present invention also provides a method for treating a disease or disorder associated with undesirable levels of angiogenesis comprising the step of: administering to a subject an effective amount of sFRP-4 or a functional equivalent thereof. More particularly the invention resides in a method of treating an angiogenic condition, said method comprising the step of: administering to a subject an anti-angiogenic effective amount of sFRP-4 or a functional equivalent thereof.

The disease or disorder may be selected from the group consisting of: cancer such as breast, prostate, brain, pancreas, lung, stomach, ovary, and cervix; leukemia, oesophagus, skin, colorectal, bladder and lymphoma, diabetic blindness, age related macular degeneration, rheumatoid arthritis, psoriasis, glaucoma, retinitis pigmentosa, obesity, synovitis, osteomyelitis, endometriosis, ovarian cysts, inflammatory bowel and periodontal disease, ascites, peritoneal adhesions, primary pulmonary hypertension, nasal polyps, asthma, warts, allergic dermatitis, Karposi sarcoma, vascular malformations, DiGeorge Syndrome, atherosclerosis and reproductive disorders such as those associated with undesirable implantation and/or fertilization.

As used herein the term "subject" will include any animal in which angiogenic activity is found to occur. Such a term includes without limitation: humans; livestock animals (such as sheep, goats, pigs, cows, horses, llamas); companion animals (such as dogs and cats); primates; birds; and fish.

The anti-angiogenesis polypeptide may be administered as a therapeutic or as a prophylactic, depending on the particular circumstances and as deemed appropriate by a medical practitioner.

Thus, the present invention also provides for the prophylactic use of sFRP-4 or a functional variant thereof to reduce or prevent angiogenesis such as that caused by a disease or disorder selected from the group consisting of: cancer such as breast, prostate, brain, pancreas, lung, stomach, ovary, and cervix; leukemia, oesophagus, skin, colorectal, bladder and lymphoma, diabetic blindness, age related macular degeneration, rheumatoid arthritis, psoriasis, glaucoma, retinitis pigmentosa, obesity, synovitis, osteomyelitis, endometriosis, ovarian cysts, inflammatory bowel and periodontal disease, ascites, peritoneal adhesions, primary pulmonary hypertension, nasal polyps, asthma, warts, allergic dermatitis, Karposi sarcoma, vascular malformations, DiGeorge Syndrome, atherosclerosis and reproductive disorders such as those associated with undesirable implantation and/or fertilization.

The route and form of administration of the formulations described herein will be by methods known to one skilled in the art, and as previously described. As one example, sFRP-4 or a functional equivalent thereof may be formulated for topical administration to reduce angiogenesis. As another example, it may be locally administered to a site to ameliorate angiogenesis. As another example, it may be administered intrathecally (brain, spinal cord, etc.). As another example, it may be administered by inhalation, through the respiratory tract (nose, trachea, bronchi, lungs, etc.). As another example, it may be instilled in a body cavity (ventricles, sinuses, bladder, etc.). As another example, it may be administered systemically.

In various embodiments, the formulations may contain other agents. The indications, effective doses, formulations, contraindications, vendors, etc. of these are available or are known to one skilled in the art. It will be appreciated that the agents include pharmaceutically acceptable salts and derivatives.

Pharmaceutical Compositions

This invention also provides pharmaceutical or veterinary compositions comprising sFRP-4 or a functional variant thereof and a pharmaceutically acceptable carrier.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

See, e.g., Remington's Pharmaceutical Sciences, 19th Ed. (1995, Mack Publishing Co., Easton, Pa.) which is herein incorporated by reference.

Pharmaceutical compositions of proteinaceous drugs of this invention are particularly useful for parenteral administration, i.e., subcutaneously, intramuscularly or intravenously. The compositions for parenteral administration will commonly comprise a solution of the compound of the invention or a cocktail thereof dissolved in an acceptable carrier, preferably an aqueous carrier. A variety of aqueous carriers may be employed, e.g., water, buffered water, 0.4% saline, 0.3% glycine, and the like. These solutions are sterile and generally free of particulate matter. These solutions may be sterilized by conventional, well known sterilization techniques. The compositions may further contain pharmaceutically acceptable auxiliary substances as required to approximate physiological conditions such as pH adjusting and buffering agents, etc.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy.

By way of illustration however, the concentration of the compound of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected. Low doses are preferred. Examples include 1-100 pg, 20-100 pg, 50-100 pg, 75-100 pg.

Thus, a pharmaceutical composition of the invention for intramuscular injection could be prepared to contain 1 ml sterile buffered water, and 50 mg of a compound of the invention. Similarly, a pharmaceutical composition of the invention for intravenous infusion could be made up to contain 250 ml of sterile Ringer's solution, and 150 mg of a compound of the invention. Actual methods for preparing parenterally administrable compositions are well known or will be apparent to those skilled in the art and are described in more detail in, for example, Remington's Pharmaceutical Science, 15th ed., Mack Publishing Company, Easton, Pa.

The compounds described herein can be lyophilized for storage and reconstituted in a suitable carrier prior to use. This technique has been shown to be effective with conventional proteins and art-known lyophilization and reconstitution techniques can be employed.

In situations where the functional variant is non-proteinaceous, it may be administered alone or in combination with pharmaceutically acceptable carriers. The proportion of the constituents in any formulation is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered sublingually in the form of troches or lozenges in which the active ingredient is mixed with sugar and corn syrups, flavouring agents and dyes; and then dehydrated sufficiently to make it suitable for pressing into a solid form. They may be administered orally in the form of solutions that may be injected parenterally, that is, intramuscularly, intravenously or subcutaneously. For parenteral administration, they may be used in the form of a sterile solution containing other solutes, for example, enough saline or glucose to make the solution isotonic.

The physician or veterinarian will determine the dosage of the present therapeutic agents that will be most suitable and it will vary with the form of administration and the particular compound chosen, and furthermore, it will vary with the particular subject under treatment. The physician will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The therapeutic dosage will generally be from 1 to 10 milligrams per day and higher although it may be administered in several different dosage units. Tablets containing from 0.5 to 10 mg of active agent are particularly useful.

As indicated above and depending on the subject's condition, the compositions of the invention can be administered for prophylactic and/or therapeutic treatments. In therapeutic application, compositions are administered to a subject suffering from an event associated with undesirable angiogenesis in an amount sufficient to overcome the adverse effects of the event. In prophylactic applications, compositions containing the sFRP-4 or a functional variant thereof are administered to a subject predisposed to a condition associated with undesirable angiogenesis to reduce the damage suffered by the subject if and when they suffer from the condition.

Single or multiple administrations of the compositions can be carried out with dose levels and pattern being selected by the treating physician or veterinarian. In any event, the composition of the invention should provide a quantity of the compounds of the invention sufficient to effectively treat the subject.

The term "pharmaceutically acceptable" means a nontoxic material that does not interfere with the effectiveness of the biological activity of the active ingredients. The characteristics of the carrier will depend on the route of administration. Pharmaceutically acceptable carriers include diluents, fillers, salts, buffers, stabilizers, solubilizers, and other materials that are well known in the art.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di- and triglycerides; hydrogel release systems; silastic systems; peptide based systems; wax coatings, compressed tablets using conventional binders and excipients, partially fused implants and the like. In addition, a pump-based hardware delivery system can be used, some of which are adapted for implantation.

A long-term sustained release implant also may be used. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. Such implants can be particularly useful in treating cancerous tumours, thereby effecting localized, high-doses of the compounds of the invention.

The present invention also provides for the use of sFRP-4 or a functional variant thereof to prepare a medicament for treating or preventing a disease or disorder characterized by undesirable angiogenesis, such as cancer such as breast, prostate, brain, pancreas, lung, stomach, ovary, and cervix; leukemia, oesophagus, skin, colorectal, bladder and lymphoma, diabetic blindness, age related macular degeneration, rheumatoid arthritis, psoriasis, glaucoma, retinitis pigmentosa, obesity, synovitis, osteomyelitis, endometriosis, ovarian cysts, inflammatory bowel and periodontal disease, ascites, peritoneal adhesions, primary pulmonary hypertension, nasal polyps, asthma, warts, allergic dermatitis, Karposi sarcoma, vascular malformations, DiGeorge Syndrome, atherosclerosis and reproductive disorders such as those associated with undesirable implantation and/or fertilization.

In an embodiment, sFRP-4 or a functional equivalent thereof is administered to a patient with one or more agent(s) known to one skilled in the art under the classification of anti-angiogenic agents and/or anti-inflammatory agents, to treat or prevent an angiogenic condition. Alternatively, the embodiment concerns the use of sFRP-4 or a functional variant thereof and an anti-angiogenic agents and/or anti-inflammatory agents, in the preparation of a medicament for treating or preventing a disease or disorder characterized by undesirable angiogenesis.

Anti-angiogenic agents that may be used in conjunction with sFRP-4 or a functional equivalent thereof include, but are not limited to, bevacizumab (rhuMab VEGF, AVASTIN®, Genentech, South San Francisco Calif.), ranibizumab (rhuFAb V2, LUCENTIS®, Genentech), pegaptanib (such as pegaptanib sodium i.e. MACUGEN®, Eyetech Pharmaceuticals, New York N.Y.), sunitinib maleate (SUTENT®, Pfizer, Groton Conn.), TNP470, integrin αv antagonists, 2-methoxyestradiol, paclitaxel, or P38 mitogen activated protein kinase inhibitors. Anti-VEGF siRNA (short double-stranded RNA to trigger RNA interference and thereby impair VEGF synthesis) may also be used as an anti-angiogenic agent.

Bevacizumab is a recombinant humanized monoclonal IgG1 antibody that binds to and inhibits the biologic activity of human VEGF in inaaa vitro and in vivo assay systems by preventing binding of VEGF with its receptor on the surface of vascular endothelial cells, thus preventing endothelial cell proliferation and new vessel formation. Bevacizumab contains human framework regions and the complementarity-determining regions of a murine antibody that binds to VEGF; it has a molecular weight of about 149 kilodaltons. Bevacizumab, by binding to VEGF, blocks VEGF from binding to receptors and thus blocks angiogenesis. Bevacizumab is typically administered by intravenous infusion, diluted in 0.9% sodium chloride for injection from a 25 mg/ml preparation, for treatment of colorectal cancer.

Ranibizumab is a derivative of the full-length antibody bevacizumab (Fab fragment), and is further modified to increase its affinity for VEGF. Both bevacizumab and ranibizumab bind all biologically active isoforms and proteolytic fragments of VEGF, but there are differences. Monovalent binding of a Fab fragment such as ranibizumab to its target antigen would not force the target to dimerize, and hence is useful to manipulate cell receptor function, but its effective antigen binding capacity is lower than its full antibody counterpart. However, VEGF, which is the desired target, is a soluble factor and not a cellular receptor. Therefore, the increased effective binding by the full length antibody bevacizumab enhances inhibition of the VEGF signal and thus provides an enhanced anti-angiogenic effect. Bevacizumab has also been "humanized" to decrease any antigenic effect it may have on the patient, and bevacizumab has a higher molecular weight; this full-length antibody likely will not penetrate the retina to the same extent as the lower molecular weight fragment ranibizumab. However, the increased size of bevacizumab may decrease its clearance rate from the site of action.

Sunitinib maleate (SUTENT®) is an orally bioavailable indolinone with potential antineoplastic activity. It blocks the tyrosine kinase activities of vascular endothelial growth factor receptor 2 (VEGFR2), platelet-derived growth factor receptor b (PDGFRb), and c-kit, thereby inhibiting angiogenesis and cell proliferation. This agent also inhibits the phosphorylation of Fms-related tyrosine kinase 3 (FLT3), another receptor tyrosine kinase expressed by some leukemic cells (NCI04). A systemic dose for cancer treatment is between 12.5 mg/day to 50 mg/day.

Anti-inflammatory agents include, but are not limited to, steroids, anti-prostaglandins, matrix metalloproteinase inhibitors, non-steroidal anti-inflammatory drugs (NSAIDS), macrolides, anti-proliferative agents, anti-cancer agents, etc. Examples of anti-inflammatory agents recognized by one skilled in the art include, but are not limited to, the following:

a. colchicine;

b. a steroid such as triamcinolone (Aristocort®; KENALOG®), anecortave acetate (RETAANE®, Alcon), betamethasone (CELESTON®), budesonide cortisone, dexamethasone DECADRON-LA®; DECADRON® phosphate; MAXIDEX® and TOBRADEX® (Alcon)), hydrocortisone methylprednisolone (DEPOMEDROL®, SOLU-MEDROL®), prednisolone (prednisolone acetate, e.g., PRED FORTE® (Allergan), Econopred and ECONOPRED PLUS® (Alcon), AK-TATE® (Akorn), PRED MILD® (Allergan), prednisone sodium phosphate (Inflamase Mild and INFLAMASE FORTE® (Ciba), METRETON® (Schering), AK-PRED® (Akorn)), fluorometholone (fluorometholone acetate (FLAREX® (Alcon), EFLONED), fluorometholone alcohol (FML® and FML-MILD®, (Allergan),FLUOR OP®), rimexolone (VEXOL®, Alcon), medrysone alcohol (HMS®, Allergan), lotoprednol etabonate (LOTEMAX® and ALREX®, Bausch & Lomb, and 11-desoxcortisol;

c. an anti-prostaglandin such as indomethacin; ketorolac tromethamine ((.+−.)-5- benzoyl-2,3-dihydro-1H-pyrrolizine-1-carboxylic acid, a compound with 2-amino-2-(hydroxymethyl)-1,3-propanediol (1:1) (ACULAR® Allegan), OCUFEN® (flurbiprofen sodium 0.03%), meclofenamate, fluorbiprofen, and the pyrrolo-pyrrole group of non-steroidal anti-inflammatory drugs;

d. a macrolide such as sirolimus (rapamycin), pimecrolimus, tacrolimus (FK506), cyclosporine (Arrestase), everolimus 40-O-(2-hydroxymethylenrapamycin), ascomycin, erythromycin, azithromycin, clarithromycin, clindamycin, lincomycin, dirithromycin, josamycin, spiramycin, diacetylmidecamycin, tylosin, roxithromycin, ABT-773, telithromycin, leucomycins, lincosamide, biolimus, ABT-578 (methyl-rapamycin), and derivatives of rapamycin such as temsirolimus (CCI-779, Wyeth) and AP23573 (Ariad);

e. a non-steroidal anti-inflammatory drug such as derivatives of acetic acid (e.g. diclofenac and ketorolac (TORADOL®, VOLTAREN®, VOLTAREN-XR®, CATAFLAM®)), salicylate (e.g., aspirin, ECOTRIN®), proprionic acid (e.g., ibuprofen (ADVIL®, MOTRIN®, MEDIPREN®, Nuprin®)), acetaminophen (TYLENOL), aniline (e.g., aminophenolacetaminophen, pyrazole (e.g., phenylbutazone), N-arylanthranilic acid (fenamates) (e.g., meclofenamate), indole (e.g., indomethacin INDOCIN®, INDOCIN-SRO®)), oxicam (e.g., piroxicam (FELDENE®)), pyrrol-pyrrole group (e.g., ACULAR), anti-platelet medications, choline magnesium salicylate (TRILISATE®), cox-2 inhibitors (meloxicam (MOBIC®)), diflunisal (DOLOBID®), etodolac (LODINE®), fenoprofen (NALFON®), flurbiprofen (ANSAID®), ketoprofen ORUDIS®), (ORUVAL®) meclofenamate (MECLOMEN®), nabumetone (RELAFEN®), naproxen (NAPROSYN®, NAPRELAN®, ANAPROX®, ALEVE®), oxaprozin (DAYPRO®), phenylbutazone (BUTAZOLIDINE®), salsalate (DISALCID®, SALFLEX®), tolmetin (TOLECTIN®), valdecoxib (BEXTRA®), sulindac (CLINORIL®), and flurbiprofin sodium (OCUFEN®)); and [0140]f. an MMP inhibitor such as doxycycline, TIMP-1, TIMP-2, TIMP-3, TIMP-4; MMP1, MMP2, MMP3, Batimastat (BB-94), TAPI-2,10-phenanthroline, and marimastat.

In a highly preferred embodiment, the method of the invention includes the step of: administering to a subject bevacizumab to treat or prevent an angiogenic condition. Bevacizumab at a dose of 5 mg/0.1 ml has been found not to be toxic. In embodiments where bevacizumab or another anti-angiogenic agent is administered in combination with sFRP-4 or a functional equivalent thereof to ameliorate an angiogenic condition, the dose of bevacizumab will range between about 0.01 mg/0.1 ml to about 5 mg/0.1 ml. Accordingly the administered dose of bevacizumab is preferably less than about 5 mg/0.1 ml. In another embodiment, the administered dose of bevacizumab ranges from 0.1 mg/ml to about 50 mg/ml. In another embodiment, the dose of bevacizumab administered systemically ranges from about 0.05 mg/ml to about 5 mg/ml. In one embodiment, the dose of bevacizumab administered topically is up to 5 mg/ml, and in another embodiment it may be higher. While these doses recite bevacizumab, one skilled in the art will appreciate that they may be used with other anti-VEGF agents, and that doses for a specific agent may be determined empirically, by patient disease severity, other patient variables, etc.

In an alternate embodiment the method of the invention includes the step of: administering to a subject ranibizumab or pegaptanib to treat or prevent an angiogenic condition. To the extent that ranibizumab is used in the method, the dose of ranibizumab (LUCENTIS®) will be about 300 or about 500 microgram doses. Alternatively, if pegaptanib (e.g. MACUGEN®) is used in the method it should be administered in a dose ranging from either about 0.3 mg to about 3.0 mg every four or six weeks.

Gene/Cell Therapy sFRP-4 or a functional variant thereof can be delivered by implanting certain cells that have been genetically engineered, using methods such as those described herein, to express and secrete the polypeptide of interest. Such cells may be animal or human cells, and may be autologous, heterologous, or xenogenic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

Additional embodiments of the present invention relate to cells and methods (e.g., homologous recombination and/or other recombinant production methods) for both the in vitro production of therapeutic polypeptides and for the production and delivery of therapeutic polypeptides by gene therapy or cell therapy. Homologous and other recombination methods may be used to modify a cell that contains a normally transcriptionally silent gene encoding a polypeptide described herein, or an under expressed gene, and thereby produce a cell which expresses therapeutically efficacious amounts of the polypeptides.

Homologous recombination is a technique originally developed for targeting genes to induce or correct mutations in transcriptionally active genes. The basic technique was developed as a method for introducing specific mutations into specific regions of the mammalian genome or to correct specific mutations within defective genes. Through homologous recombination, a given DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process.

It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome. Attached to these pieces of targeting DNA are regions of DNA that may interact with or control the expression of a polypeptide herein, e.g., flanking sequences. For example, a promoter/enhancer element, a suppresser or an exogenous transcription modulatory element is inserted in the genome of the intended host cell in proximity and orientation sufficient to influence the transcription of DNA encoding the desired polypeptide. The control element controls a portion of the DNA present in the host cell genome. Thus, the expression of the desired polypeptide of the present invention may be achieved not by transfection of DNA that encodes the polypeptide itself, but rather by the use of targeting DNA (containing regions of homology with the endogenous gene of interest), coupled with DNA regulatory segments that provide the endogenous gene sequence with recognizable signals for transcription of the gene encoding the polypeptide.

In an exemplary method, the expression of a gene encoding sFRP-4 or a functional variant thereof in a cell (i.e., a desired endogenous cellular gene) is altered via homologous recombination into the cellular genome at a preselected site, by the introduction of DNA that includes at least a regulatory sequence, an exon and a splice donor site. These components are introduced into the chromosomal (genomic) DNA in such a manner that this, in effect, results in the production of a new transcription unit (in which the regulatory sequence, the exon and the splice donor site present in the DNA construct are operatively linked to the endogenous gene). As a result of the introduction of these components into the chromosomal DNA, the expression of the desired endogenous gene is altered.

Altered gene expression, as described herein, encompasses activating (or causing to be expressed) a gene which is normally silent (unexpressed) in the cell, as well as increasing the expression of a gene which is not expressed at physiologically significant levels in the cell. The embodiments further encompass changing the pattern of regulation or induction such that it is different from the pattern of regulation or induction that occurs in the cell, and reducing (including eliminating) the expression of a gene which is expressed in the cell.

One method by which homologous recombination can be used to increase, or cause production of a polypeptide described herein from a cell's endogenous gene involves first using homologous recombination to place a recombination sequence from a site-specific recombination system (e.g., Cre/loxP, FLP/FRT) (see, Sauer, Current Opinion In Biotechnology, 5:521-527, 1994; and Sauer, Methods In Enzymology, 225:890-900, 1993) upstream (that is, 5' to) of the cell's endogenous genomic polypeptide coding region. A plasmid containing a recombination site homologous to the site that was placed just upstream of the genomic polypeptide coding region is introduced into the modified cell line along with the appropriate recombinase enzyme. This recombinase enzyme causes the plasmid to integrate, via the plasmid's recombination site, into the recombination site located just upstream of the genomic polypeptide coding region in the cell line (Baubonis and Sauer, Nucleic Acids Res., 21:2025-2029, 1993; and O'Gorman et al., Science, 251: 1351-1355, 1991). Any flanking sequences known to increase transcription (e.g., enhancer/promoter, intron or translational enhancer), if properly positioned in this plasmid, would integrate in such a manner as to create a new or modified transcriptional unit resulting in de novo or increased polypeptide production from the cell's endogenous gene.

A further method is to use the cell line in which the site-specific recombination sequence has been placed just upstream of the cell's endogenous genomic polypeptide coding region is to use homologous recombination to introduce a second recombination site elsewhere in the cell line's genome. The appropriate recombinase enzyme is then introduced into the two-recombination-site cell line, causing a recombination event (deletion, inversion or translocation) (Sauer, Current Opinion In Biotechnology, supra, 1994 and Sauer, Methods In Enzymology, supra, 1993) that would create a new or modified transcriptional unit resulting in de novo or increased polypeptide production from the cell's endogenous gene.

Another approach for increasing, or causing, the expression of the polypeptide from a cell's endogenous gene involves increasing, or causing, the expression of a gene or genes (e.g., transcription factors) and/or decreasing the expression of a gene or genes (e.g., transcriptional repressors) in a manner which results in de novo or increased polypeptide production from the cell's endogenous gene. This method includes the introduction of a non-naturally occurring polypeptide (e.g., a polypeptide comprising a site-specific DNA binding domain fused to a transcriptional factor domain) into the cell such that de novo or increased polypeptide production from the cell's endogenous gene results.

The present invention further relates to DNA constructs useful in the method of altering expression of a target gene. In certain embodiments, the exemplary DNA constructs comprise: (a) one or more targeting sequences; (b) a regulatory sequence; (c) an exon; and (d) an unpaired splice-donor site. The targeting sequence in the DNA construct directs the integration of elements (a)-(d) into a target gene in a cell such that the elements (b)-(d) are operatively linked to sequences of the endogenous target gene. In another embodiment, the DNA constructs comprise: (a) one or more targeting sequences, (b) a regulatory sequence, (c) an exon, (d) a splice-donor site, (e) an intron, and (f) a splice-acceptor site, wherein the targeting sequence directs the integration of elements (a)-(f) such that the elements of (b)-(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence of the polypeptides presented herein, a piece of DNA that is complementary to a selected region of the gene can be synthesized or otherwise obtained, such as by appropriate restriction of the native DNA at specific recognition sites bounding the region of interest. This piece serves as a targeting sequence(s) upon insertion into the cell and will hybridize to its homologous region within the genome. If this hybridization occurs during DNA replication, this piece of DNA, and any additional sequence attached thereto, will act as an Okazaki fragment and will be incorporated into the newly synthesized daughter strand of DNA. The present invention, therefore, includes nucleotides encoding a polypeptide, which nucleotides may be used as targeting sequences.

Polypeptide cell therapy, e.g., the implantation of cells producing polypeptides described herein, is also contemplated. This embodiment involves implanting cells capable of synthesizing and secreting a biologically active form of the polypeptide. Such polypeptide-producing cells can be cells that are natural producers of the polypeptides or may be recombinant cells whose ability to produce the polypeptides has been augmented by transformation with a gene encoding the desired polypeptide or with a gene augmenting the expression of the polypeptide. Such a modification may be accomplished by means of a vector suitable for delivering the gene as well as promoting its expression and secretion. In order to minimize a potential immunological reaction in patients being administered a polypeptide, as may occur with the administration of a polypeptide of a foreign species, it is preferred that the natural cells producing polypeptide be of human origin and produce human polypeptide. Likewise, it is preferred that the recombinant cells producing polypeptide be transformed with an expression vector containing a gene encoding a human polypeptide.

Implanted cells may be encapsulated to avoid the infiltration of surrounding tissue or deleterious immune responses from the subject. Human or non-human animal cells may be implanted in patients in biocompatible, semipermeable polymeric enclosures or in membranes that allow the release of polypeptide, but prevent the destruction of the cells by the patient's immune system or by other detrimental factors from the surrounding tissue. Alternatively, the patient's own cells, transformed to produce polypeptides ex vivo, may be implanted directly into the patient without such encapsulation.

Techniques for the encapsulation of living cells are known in the art, and the preparation of the encapsulated cells and their implantation in patients may be routinely accomplished. For example, Baetge et al. (WO 95/05452 and PCT/US94/09299) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operatively linked to promoters that are not subject to down-regulation in vivo upon implantation into a mammalian host. The devices provide for the delivery of the molecules from living cells to specific sites within a recipient. A system for encapsulating living cells is described in PCT Application PCT/US91/00157 of Aebischer et al. See also, PCT Application PCT/US91/00155 of Aebischer et al.; Winn et al., Exper. Neurol., 113:322-329 (1991), Aebischer et al., Exper. Neurol., 111:269-275 (1991); and Tresco et al., ASAIO, 38:17-23 (1992).

In vivo and in vitro gene therapy delivery of polypeptides is also part of the present invention. One example of a gene therapy technique is to use the gene (either genomic DNA, cDNA, and/or synthetic DNA) encoding a polypeptide described herein that may be operably linked to a constitutive or inducible promoter to form a "gene therapy DNA construct". The promoter may be homologous or heterologous to the endogenous gene, provided that it is active in the cell or tissue type into which the construct will be inserted. Other components of the gene therapy DNA construct may optionally include, DNA molecules designed for site-specific integration (e.g., endogenous sequences useful for homologous recombination); tissue-specific promoter, enhancer(s) or silencer(s); DNA molecules capable of providing a selective advantage over the parent cell; DNA molecules useful as labels to identify transformed cells; negative selection systems, cell specific systems; cell-specific binding agents (as, for example, for cell targeting); cell specific internalization factors; and transcription factors to enhance expression by a vector, as well as factors to enable vector manufacture.

A gene therapy DNA construct can then be introduced into cells (either ex vivo or in vivo) using viral or non-viral vectors. Certain vectors, such as retroviral vectors, will deliver the DNA construct to the chromosomal DNA of the cells, and the gene can integrate into the chromosomal DNA. Other vectors will function as episomes, and the gene therapy DNA construct will remain in the cytoplasm.

In yet other embodiments, regulatory elements can be included for the controlled expression of the gene in the target cell. Such elements are turned on in response to an appropriate effector. In this way, a therapeutic polypeptide can be expressed when desired. One conventional control means involves the use of small molecule dimerizers or rapalogs (as described in WO 9641865 (PCT/US96/099486); WO 9731898 (PCT/US97/03137) and WO9731899 (PCT/US95/03157) used to dimerize chimeric proteins which contain a small molecule-binding domain and a domain capable of initiating biological process, such as a DNA-binding protein or a transcriptional activation protein. The dimerization of the proteins can be used to initiate transcription of the transgene.

An alternative regulation technology uses a method of storing proteins expressed from the gene of interest inside the cell as an aggregate or cluster. The gene of interest is expressed as a fusion protein that includes a conditional aggregation domain that results in the retention of the aggregated protein in the endoplasmic reticulum. The stored proteins are stable and inactive inside the cell. The proteins can be released, however, by administering a drug (e.g., small molecule ligand) that removes the conditional aggregation domain and thereby specifically breaks apart the aggregates or clusters so that the proteins may be secreted from the cell.

Another control means uses a positive tetracycline-controllable transactivator. This system involves a mutated tet repressor protein DNA-binding domain (mutated tet R-4 amino acid changes which resulted in a reverse tetracycline-regulated transactivator protein, i.e., it binds to a tet operator in the presence of tetracycline) linked to a polypeptide that activates transcription.

In vivo gene therapy may be accomplished by introducing the gene encoding a polypeptide into cells via local injection of a nucleic acid molecule or by other appropriate viral or non-non-viral delivery vectors. For example, a nucleic acid molecule encoding a polypeptide of the present invention may be contained in an adeno-associated virus (AAV) vector for delivery to the targeted cells (e.g., Johnson, International Publication No. WO95/34670; and International Application No. PCT/US95/07178). The recombinant AAV genome typically contains AAV inverted terminal repeats flanking a DNA sequence encoding a polypeptide operably linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells that have been treated in vitro to insert a DNA segment encoding a therapeutic protein. Additional methods and materials for the practice of gene therapy techniques are described in U.S. Pat. No. 5,631,236 involving adenoviral vectors; U.S. Pat. No. 5,672,510 involving retroviral vectors; and U.S. Pat. No. 5,635,399 involving retroviral vectors expressing cytokines.

Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include the use of inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. Pat. No. 4,970,154 involving electroporation techniques; WO96/40958 involving nuclear ligands; U.S. Pat. No. 5,679,559 describing a lipoprotein-containing system for gene delivery; U.S. Pat. No. 5,676,954 involving liposome carriers; U.S. Pat. No. 5,593,875 concerning methods for calcium phosphate transfection; and U.S. Pat. No. 4,945,050 wherein biologically active particles are propelled at cells at a speed whereby the particles penetrate the surface of the cells and become incorporated into the interior of the cells.

It is also contemplated that gene therapy or cell therapy according to the present invention can further include the delivery of one or more additional polypeptide(s) in the same or a different cell(s). Such cells may be separately introduced into the patient, or the cells may be contained in a single implantable device, such as the encapsulating membrane described above, or the cells may be separately modified by means of viral vectors.

A means to increase endogenous polypeptide expression in a cell via gene therapy is to insert one or more enhancer element into the polypeptide promoter, where the enhancer element(s) can serve to increase transcriptional activity of the gene. The enhancer element(s) used will be selected based on the tissue in which one desires to activate the gene(s); enhancer elements known to confer promoter activation in that tissue will be selected. Here, the functional portion of the transcriptional element to be added may be inserted into a fragment of DNA containing the polypeptide promoter (and optionally, inserted into a vector and/or 5' and/or 3' flanking sequence(s), etc.) using standard cloning techniques. This construct, known as a "homologous recombination construct", can then be introduced into the desired cells either ex vivo or in vivo.

Gene therapy also can be used to decrease polypeptide expression by modifying the nucleotide sequence of the endogenous promoter(s). Such modification is typically accomplished via homologous recombination methods. For example, a DNA molecule containing all or a portion of the promoter of the gene selected for inactivation can be engineered to remove and/or replace pieces of the promoter that regulate transcription. For example the TATA box and/or the binding site of a transcriptional activator of the promoter may be deleted using standard molecular biology techniques; such deletion can inhibit promoter activity thereby repressing the transcription of the corresponding gene. The deletion of the TATA box or the transcription activator binding site in the promoter may be accomplished by generating a DNA construct comprising all or the relevant portion of the polypeptide promoter(s) (from the same or a related species as the polypeptide gene to be regulated) in which one or more of the TATA box and/or transcriptional activator binding site nucleotides are mutated via substitution, deletion and/or insertion of one or more nucleotides. As a result, the TATA box and/or activator binding site has decreased activity or is rendered completely inactive. The construct will typically contain at least about 500 bases of DNA that correspond to the native (endogenous) 5' and 3' DNA sequences adjacent to the promoter segment that has been modified. The construct may be introduced into the appropriate cells (either ex vivo or in vivo) either directly or via a viral vector as described herein. Typically, the integration of the construct into the genomic DNA of the cells will be via homologous recombination, where the 5' and 3' DNA sequences in the promoter construct can serve to help integrate the modified promoter region via hybridization to the endogenous chromosomal DNA.

Methods of Identifying sFRP-4 Receptors

The present invention also provides a method of identifying an endothelial cell sFRP-4 receptor comprising the steps of: (i) contacting an endothelial cell or extract thereof with sFRP-4; (ii) isolating any complexes including sFRP-4 and a receptor; and (iii) characterising the receptor.

Assays for assessing the binding ability of sFRP-4 to endothelial cells include the following techniques: coimmunoprecipitation; reporter gene assays; electrophoretic mobility shift assay (EMSA); and Fret/Bret assays.

The yeast 2 hybrid system could also be used to study sFRP-4-endothelial cell receptor interactions in a semi in vivo system. Yeast 2 hybrid involves the subcloning of the genes of the proteins in question into vectors with a portion of a transcriptional activator of a reporter gene (usually fluorescent gene like beta-Gal or Lex A). The DNA binding domain is on one vector while the activation domain is on the other vector. Each protein is subcloned into both vectors, and then these vectors are transformed in to yeast with the reporter gene already present. Important controls for this assay are autoactivation testing where gene+binding domain are transformed with empty activation domain to confirm the protein does not activate transcription itself. Autoactivation can be worked around by only having that gene in the activation domain vector. Autoactivation with the gene binding to the DNA sequence the binding domain interacts with is not tested due the sequence specificity of the DNA binding domain. Each vector will have a different growth advantage such that initial transforms will for example grow on -Leucine and -Tryptophan plates. Colonies are picked from these plates and transferred to a second reporter plate which is usually -Histidine. Only cells with the transformed proteins interacting will acquire the histidine growth advantage. These colonies are then picked and their fluorescence confirmed to insure no false positive growth.

This system also enables for testing how mutations in known protein interactions disrupt their binding. For mutation testing, the reporter gene is usually replaced by a death gene in which only non interacting protein systems leave the cell alive. Yeast 3 hybrids are also performed where a chaperone is necessary for the major protein-protein interaction, but it is far less popular a test. The assay may also be performed in conjunction will other interaction assays like GST pulldown or immunofluorescence.

Non-Limiting Illustration of the Invention

Further features of the present invention are more fully described in the following non-limiting Examples. This description is included solely for the purposes of exemplifying the present invention. It should not be understood as a restriction on the broad description of the invention as set out above.

EXAMPLE 1 sFRP-4 has Anti-Angiogenic Properties

Materials/Methods: Wound Healing is a Method to Assess the Cell Migration.

Trypsinized ECV-304 cells in 1 ml of DMEM/10% FBS were seeded in a 24-well plate. Twenty-four hours later when the cells reached confluence, scratching the monolayer with a 1 mm wide sterile plastic scraper a linear wound was made. After washing with 1×PBS, the cells were incubated at 37° C./5% CO2 for one hour with different concentrations (0, 125, 250 and 500 pg/ml) sFRP-4. Bright field microscopy images were taken with 4× and 40× objectives respectively. Under 40× magnification we categorically observed the migration pattern of the cells on the wound edges along with the migration rate.

Results

Figure 2B:
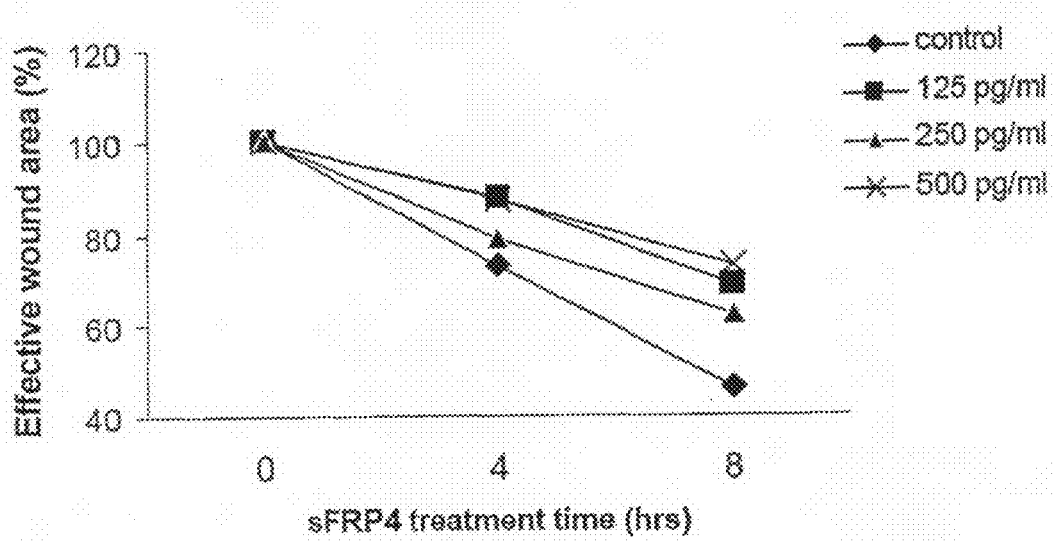
FIG. 2B—Graph quantitating results depicted in FIG. 2A. Conclusion from previous images was confirmed by measuring the wound using ImageJ software. Wound healing was inhibited following sFRP-4 treatment. (n=5). *Significantly different from control group. ($p<0.05$)
Figure 2C:
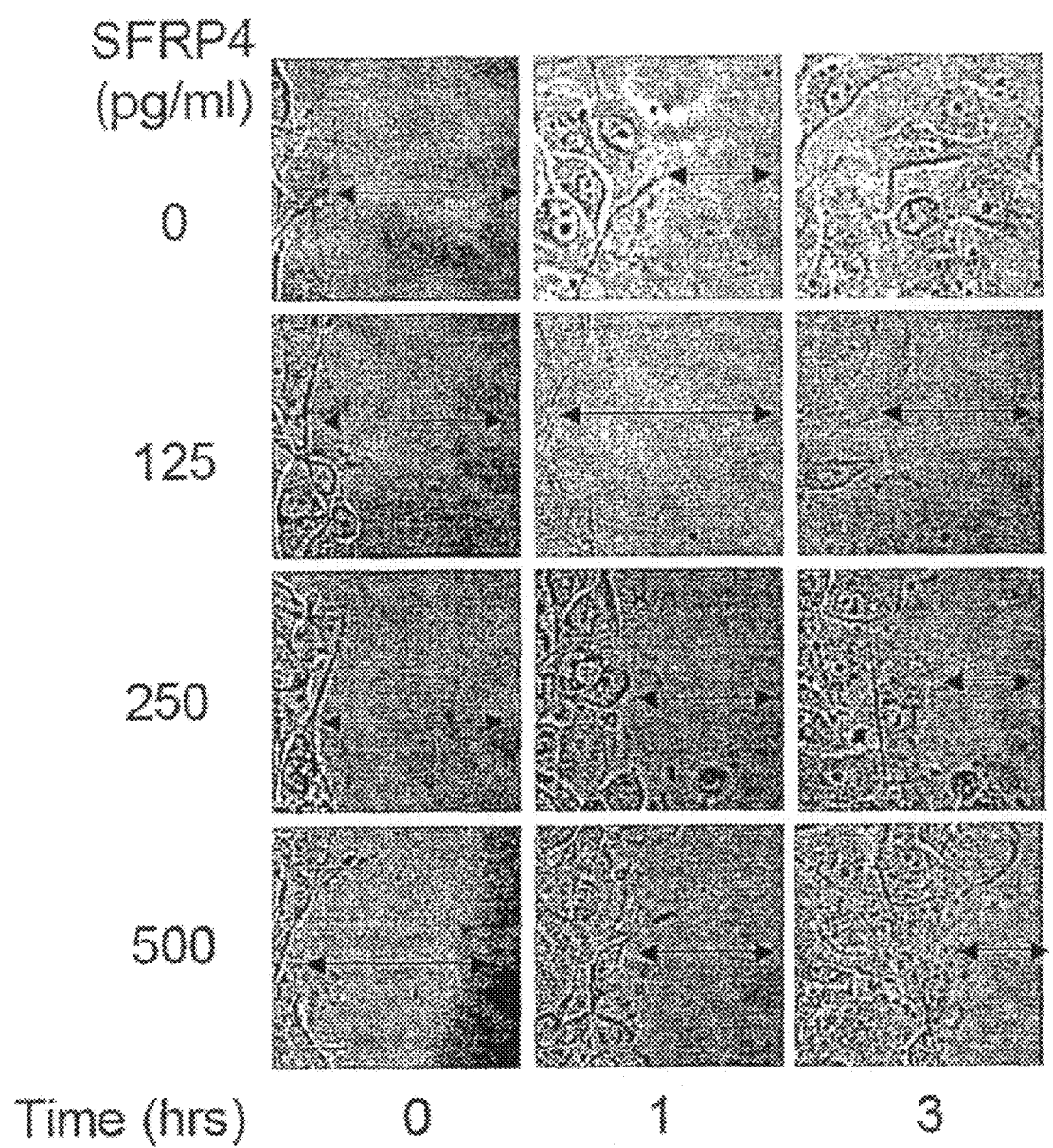
FIG. 2C—Microscopy images showing the results of the wound healing assay (4× and 40× magnification) with different concentrations of sFRP-4. Dose dependent effect of sFRP-4 on ECV304 cells. Result suggested that 125 pg/ml concentration was most effective concentration for sFRP-4 in cell based assays.
Figure 2D:
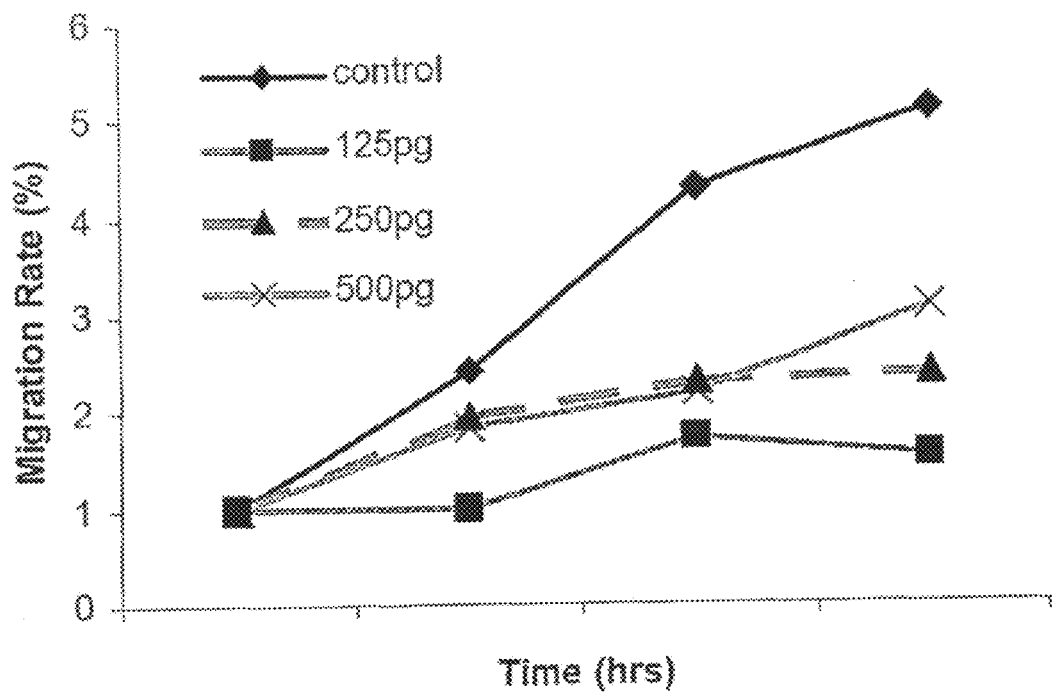
FIG. 2D—Graph quantitating results depicted in FIG. 2C. Wound healing was measured using ImageJ software. Result suggested that 125 pg/ml concentration was most effective concentration for sFRP-4 in cell based assays. n=5. *Statistical analysis showed significant difference from control set. ($p<0.05$)

A regression in wound healing capabilities of ECV-304 cell under sFRP-4 treatment is clearly evident (FIGS. 2A and 2B). A 50% reduction in wound-healing pattern after 125 pg/ml sFRP-4 treated ECV-304 cells is observed when compared to the control (FIG. 2B). The results indicated in FIGS. 2C and 2D that sFRP-4 blocks wound healing by preventing filopodia and lamilopodia formation. The difference is evident from the graphical representation of the wound area ratio (FIG. 2D).

Figure 2E:
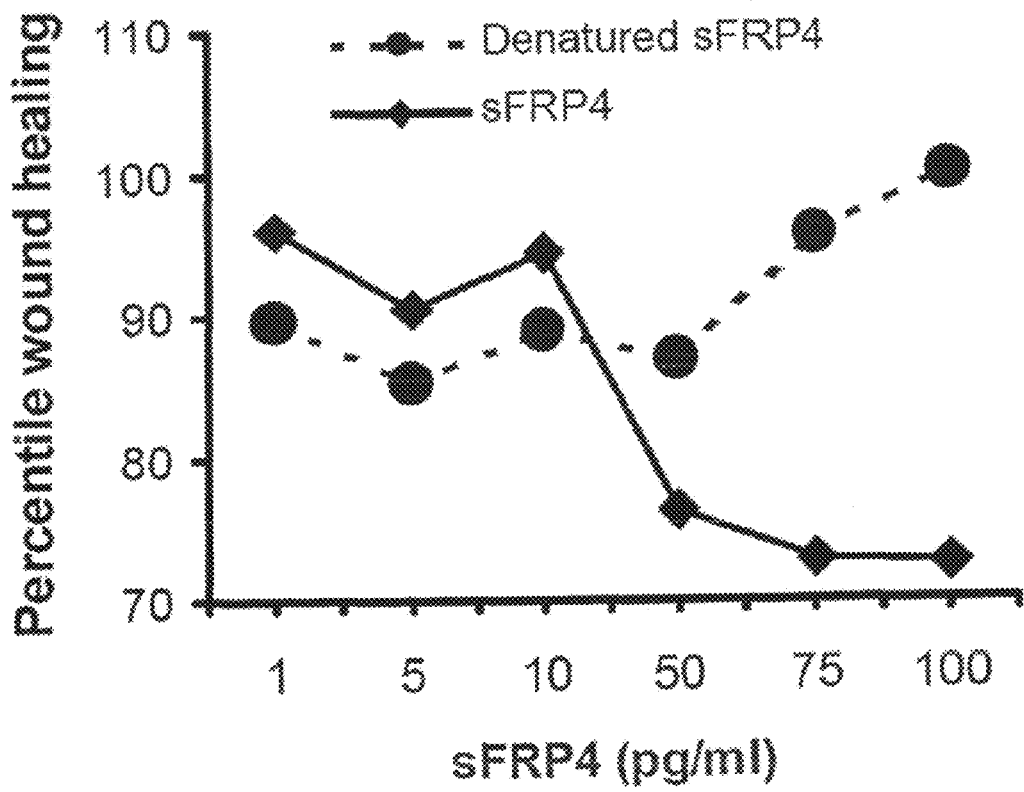
FIG. 2E—Graph showing dose response curve for sFRP-4 in relation to wound healing. Inhibition of wound healing by sFRP-4 is a dose dependent phenomenon. Result depicts 125 pg is most effective concentration.

Dose dependent effect of sFRP-4 on wound healing of endothelial mono-layer is described in FIG. 2E. FIG. 2E further depicts that 50 pg/ml sFRP-4 is the threshold concentration, which restricts wound healing in endothelial monolayer.

EXAMPLE 2 sFRP-4 Inhibits Migration

Materials/Methods

Trypsinized ECV 304 cells in suspension were used for migration assay using Boyden's chamber, which is a two chamber system. A collagen coated 8-μm pore size polycarbonate membrane separates the upper and lower chambers. ECV 304 cells were loaded in the upper well with sFRP-4 alone or sFRP-4 plus SNP. The lower well was filled with DMEM. The chambers were then incubated at 37° C./5% CO2 for 3 hrs. Cells migrated across the membrane and stuck to the lower part of the membrane. After the incubation, the polycarbonate membrane was fixed and stained with propidium iodide, a fluorescent nuclear probe. Endothelial cell migration activity was quantified as the number of migrated cells on the lower surface of the membrane.

Results

Figure 3:
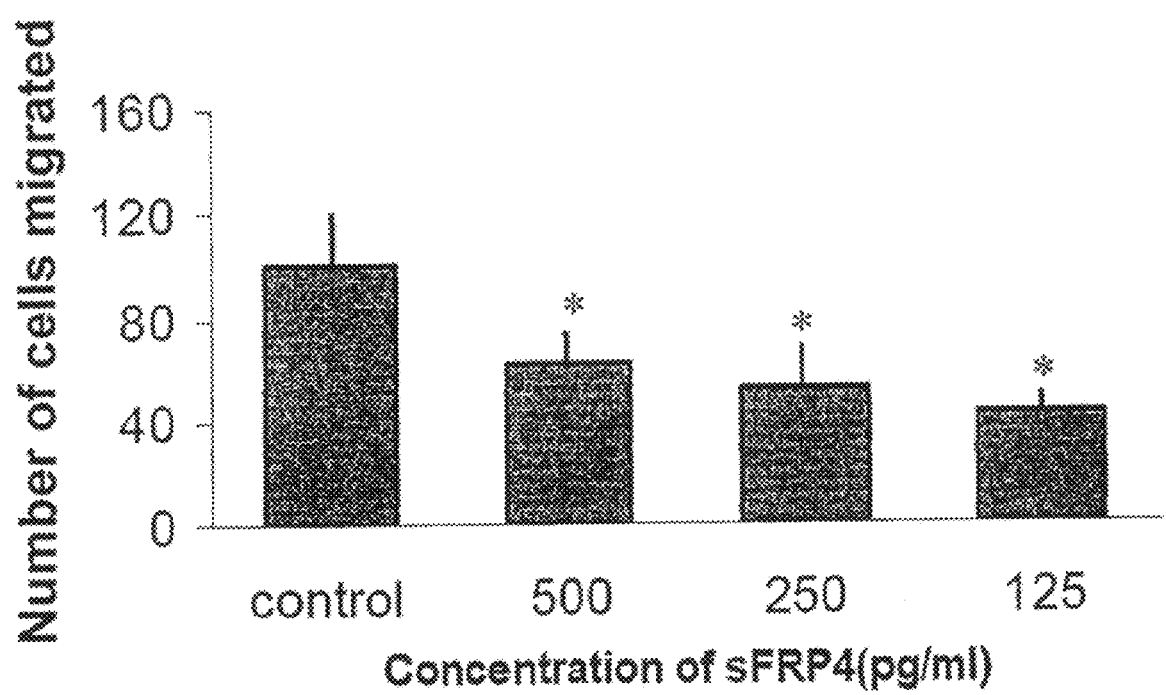
FIG. 3—Graph illustrating results of cell migration assay (Boyden's chamber based migration assay) at different sFRP-4 concentrations. Boyden's chamber assay was performed to check the migration pattern of ECV304 cells following sFRP-4 treatment. Migration of ECV304 was inhibited by sFRP-4. (n=8) *Significantly different from control set ($p<0.05$)

The migration of ECV cells across the membrane was reduced to up to 50% under sFRP-4 treatment evident from FIG. 3.

EXAMPLE 3 sFRP-4 Inhibits Tube Formation in Endothelial Cells

Materials/Methods

Figure 4A:
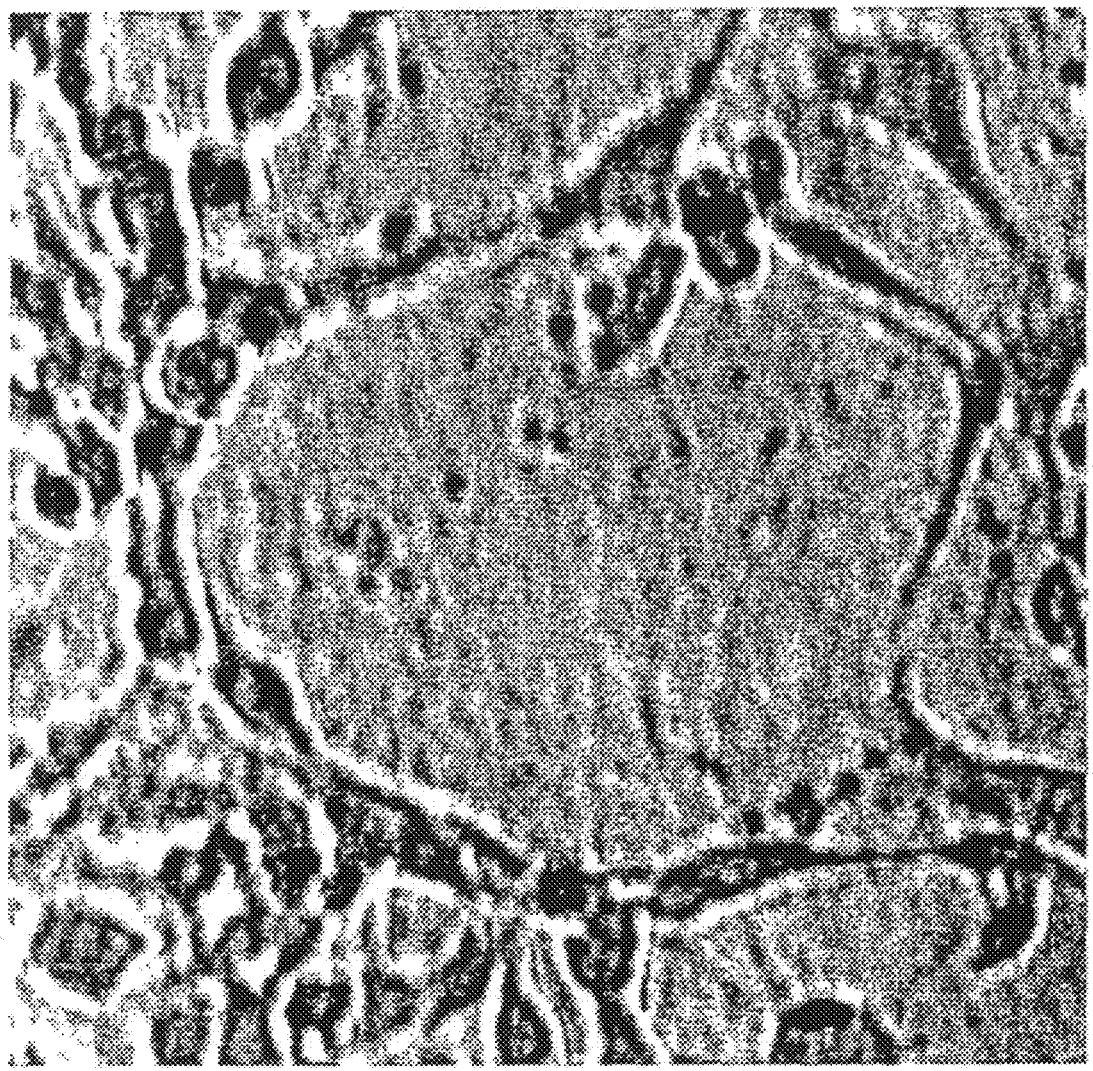
FIG. 4A—Microscope image of ring formation. Representative image of ring.
Figure 4B:
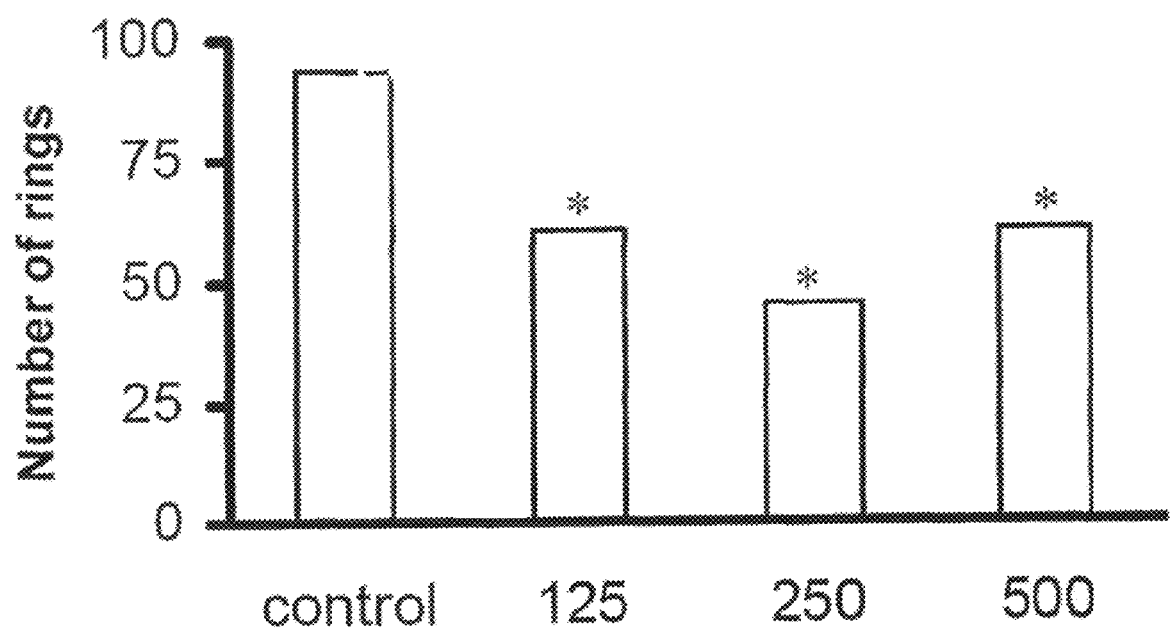
FIG. 4B—Graph illustrating dose response curve for sFRP-4 in relation to ring formation. Ring formation following sFRP-4 treatment was examined. Ring formation by ECV304 cells was inhibited by sFRP-4 treatment. (n=3). *Significantly different from control set. ($p<0.05$)

ECV304 cells in monolayer (FIG. 4A) were trypsinized and seeded on 12-well plates with 60% cell density. After a period of 7 hrs incubation, the cells were treated with different concentrations sFRP-4 (125, 250 and 500 pg/ml), incubated in 37° C./5% $CO_2$ for 18-20 hrs and counted for number of tubes formed (FIG. 4B).

Results

The graph indicates a remarkable drop (30% in 125 pg/ml, 40% 250 pg/ml and 20% in 500 pg/ml) in the number of rings formed by ECV cells under the treatment of sFRP-4, when compared to the control.

EXAMPLE 4 sFRP-4 Decreases Nitric Oxide Production in Endothelial Cells

Figure 5:
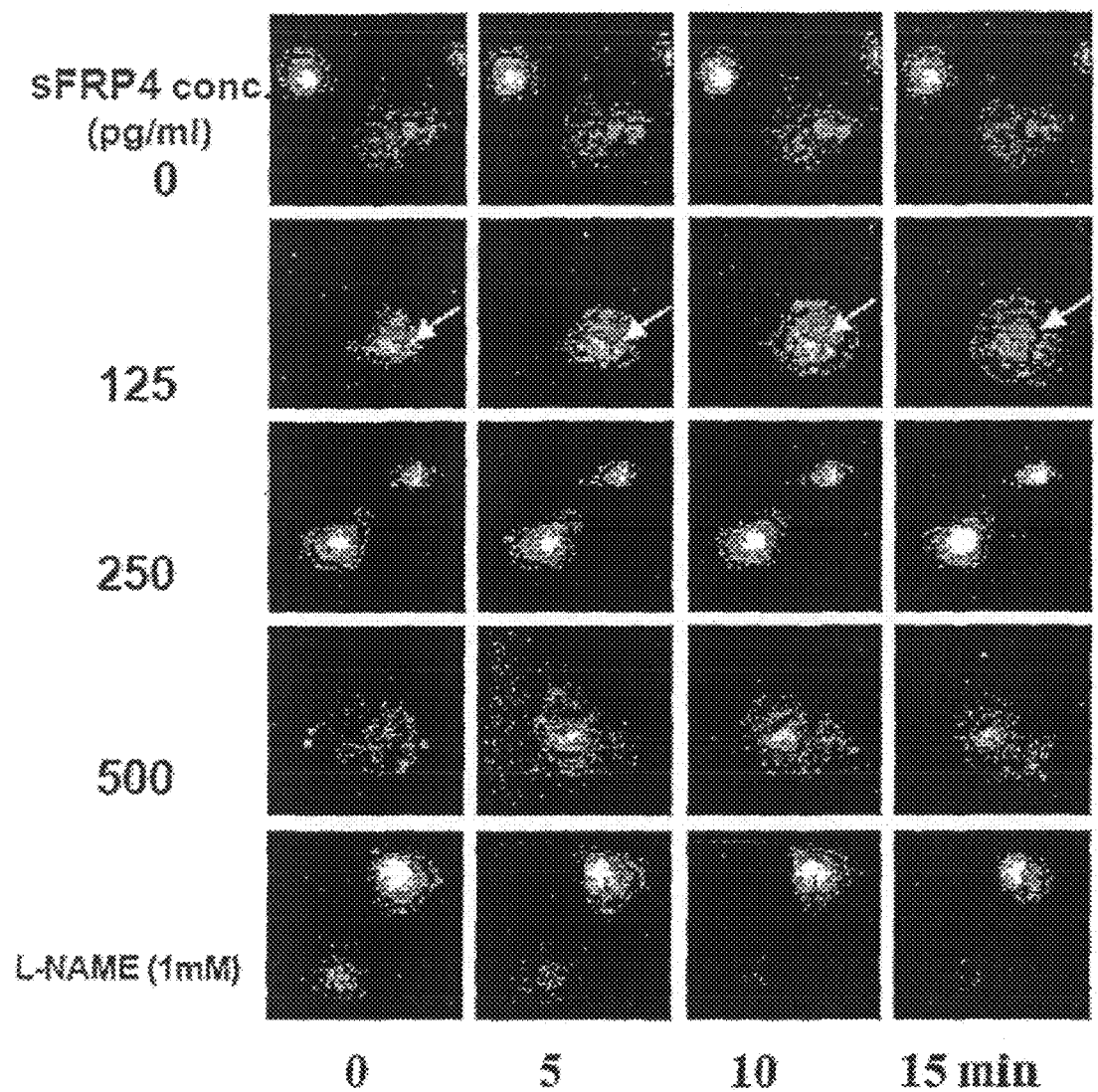
FIG. 5—Images showing fluorescent intensity of nitric oxide (NO) production at various concentrations of sFRP-4. sFRP-4 significantly reduced NO production.

Materials/Methods eNOS over-expressed ECs cultured on cover glasses in 12 well plates were taken and incubated with different concentrations (125, 250 and 500 pg/ml) sFRP-4. Before the experiments, cells were washed twice with 1×PBS (phosphate buffered saline, pH 7.4) and then loaded with 200 μl DAF-2DA (10 μM) and incubated for 5 min. After another incubation of 5 min with 1 μM calcium ionophore (which allows calcium to impregnate into the cells by creating ion channels), cells were stimulated with 500 μM calcium chloride and effects were observed under the NIKON fluorescence microscope at 515 nm. Images were taken with a CCD camera attached to it (see FIG. 5).

Results

Quantification of fluorescence intensity of DAF-NO reveals that 125 pg/ml sFRP-4 treatment attenuated calcium dependent nitric oxide production by 70%.

EXAMPLE 5 sFRP-4 Decreases the Permeability of Endothelial Cells

Materials/Methods

Membrane permeability of ECV-304 cells was measured by tracking the nuclear staining pattern of the cells using trypan blue. ECs grown on cover glasses in 12 well plates were incubated with varied concentrations of sFRP-4 (125, 250 and 500 pg/ml), at 37° C./5% CO2. Mounting the cover glasses in a live-cell chamber, phase contrast images with 6 sec time-lapse were taken at 40× magnification after addition of trypan blue (0.004%). Intensity of the nucleus was measured using an analyzing software Adobe photoshop ver. 7.0 (see FIG. 6).

Results

Figure 6:
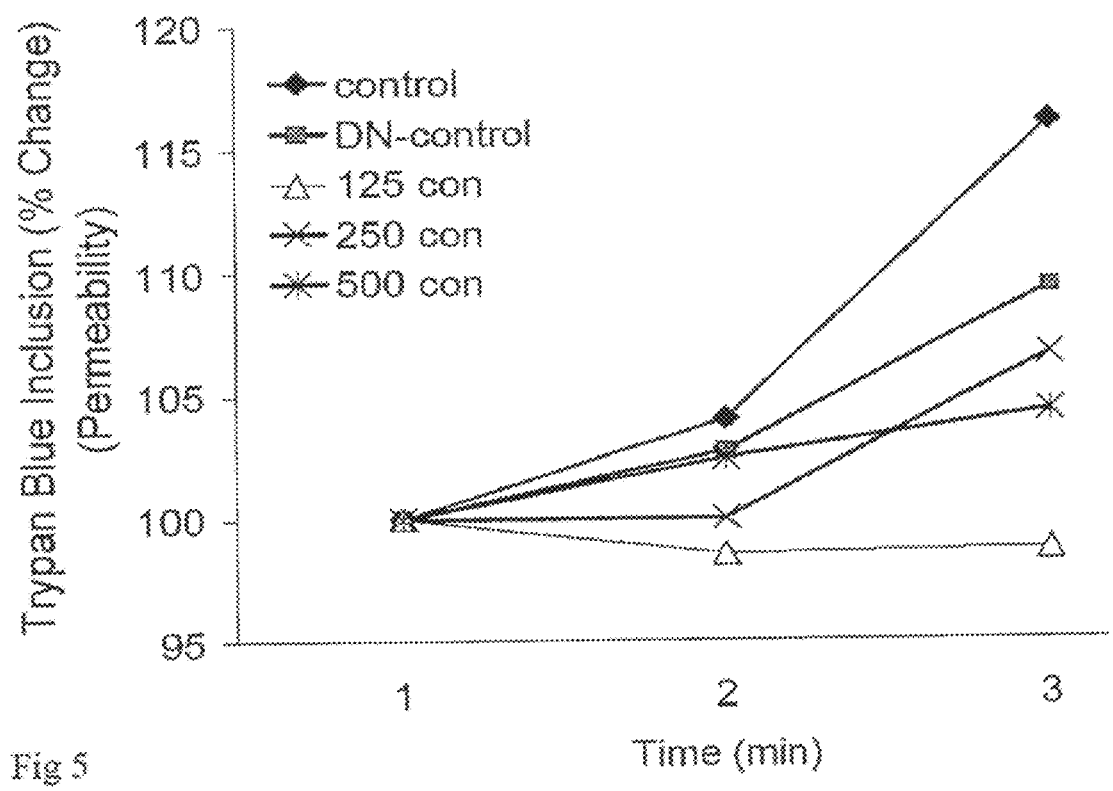
FIG. 6—Graph illustrating dose response curve for sFRP-4 in relation to permeability (Trypan blue inclusion studies). In order to check the monolayer permeability pattern of ECV304 cells following sFRP-4 treatment, monolayer permeability assay (using trypan blue) was performed. With increasing concentration of sFRP-4. The leakiness of ECV304 monolayer increased with sFRP-4, an indication that cells were more permeable under sFRP-4 treatment. (n=3). *Difference from control was statistically significant. ($p<0.05$)

FIG. 6 shows that the intensity of nuclear staining by trypan blue reduces by 15 to 20% in sFRP4 treated cells, indicating a considerable decrease in the permeability of plasma membrane of ECV-304 cells under sFRP-4 treatment.

EXAMPLE 6

Effect of sFRP-4 on Ring Formation in Endothelial Monolayers

Materials/Methods

ECV304 cells were seeded onto collagen coated plates and incubated overnight at 37° C./5% $CO_2$. The formation of ring structures was observed microscopically after 12 hrs of incubation. Next, the rings were treated with 125 pg/ml of sFRP-4 and imaged for 15 min at 5 min intervals. A control was run with rings treated with vehicle only.

Results

Figure 7:
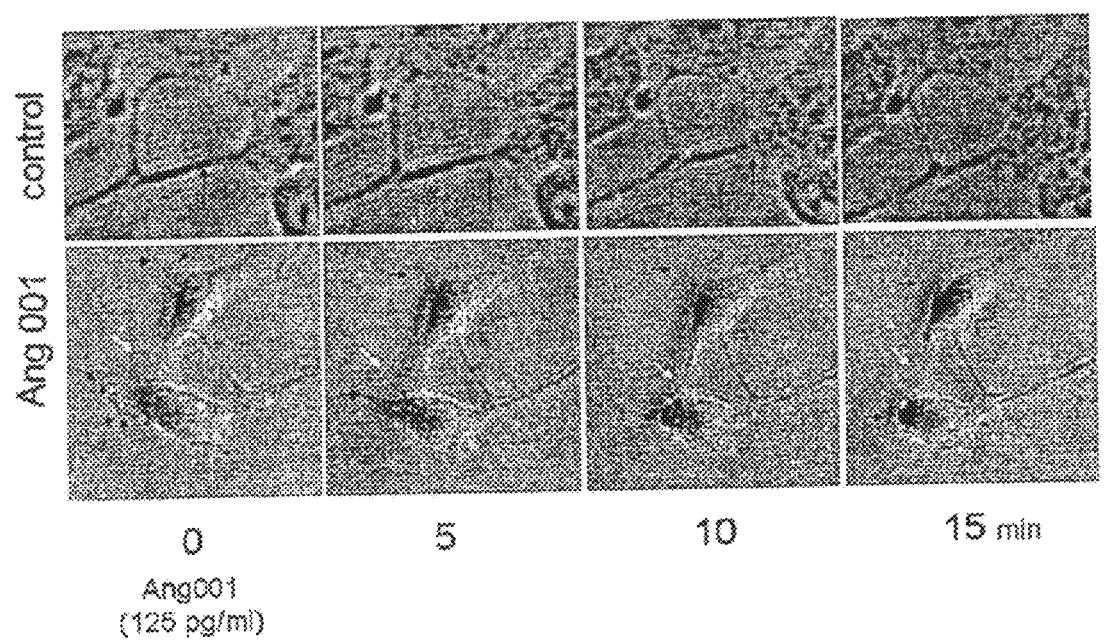
FIG. 7—Effect of sFRP-4 on ring formation in endothelial monolayers. ECV cells were seeded in 24 well plates, and cells were incubated overnight at 37° C./5% $CO_2$. After 22 hrs the tube structures were formed in the endothelial monolayers. Individual ring was focused under microscope. Next, the ring was treated with sFRP-4 (125 pg/ml) for 15 minutes. A time-lapse recording of the rings under Ang001 treatment was taken. Using vehicle only another set of control experiments was performed. Result suggested that sFRP-4 destabilized the integration of the ring. The experiments were performed in triplicates (n=3).

Ring formation and its stability in monolayer of endothelial cells represent angiogenesis in cell based models. Present result suggests that preformed rings are not stable under sFRP4 treatment (see FIG. 7).

EXAMPLE 7

Lamellipodia Assay

Materials/Methods

ECV304 cells were seeded onto 24 well plates and incubated overnight at 37° C./5% $CO_2$. Using phase contrast microscopy single cells were identified and observed during treatment with 125 pg/ml sFRP-4. The cells were imaged for 15 minutes at 5 min intervals. A control was performed using cells treated with vehicle only. The number of lamellipodia developing from the observed single cells was counted using photo analysis software.

Results

Figure 8:
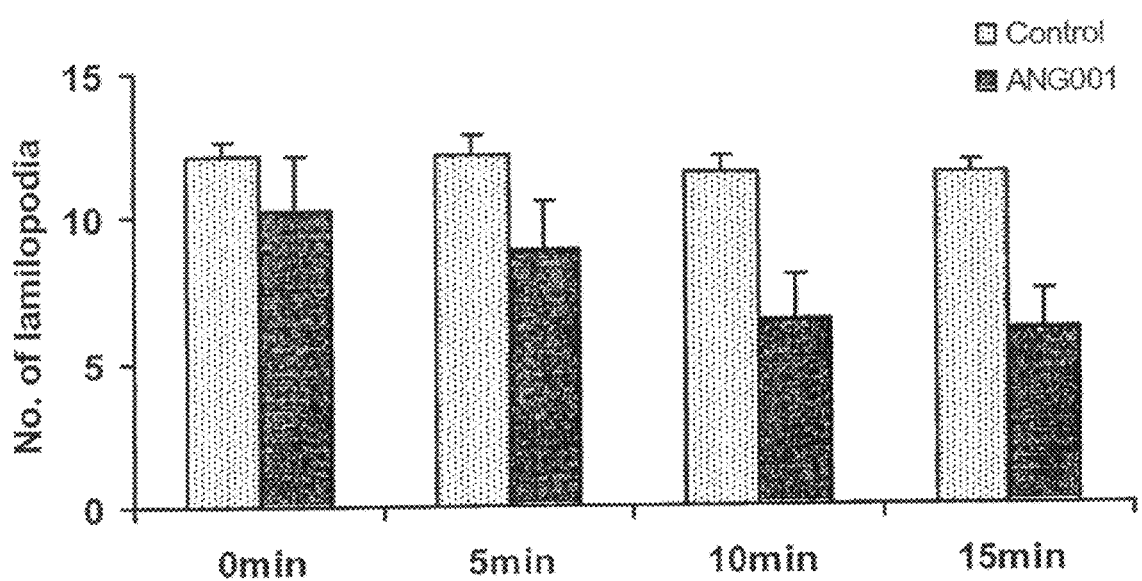
FIG. 8—Depicts results from lamellipodia assays using sFRP-4. Number of lamellipodia was counted following sFRP-4 treatment. Result suggests that the number of lamellipodia decreases following sFRP-4 treatment. (n=5). *Significantly different from control sets. ($p<0.05$)

Formation of lamellipodia is the initial step of cellular migration, which in turn is the initiation point for angiogenesis. Results depict that sFRP-4 blocks lamellipodia formation in endothelial cells (see FIG. 8).

EXAMPLE 8

Scratch Wound Assay & Avastin

Materials/Methods

EAhy926 cells were seeded onto a 24 well plate and incubated overnight at 37° C./5% $CO_2$. A scratch wound was created in monolayer of cells and 0h images of the wound was taken. Next, cells were treated with 500 pg/ml Avastin or 125 pg/ml sFRP-4. After 4 h and 8 h of treatment, images of the wounds were taken. Next, media was removed from each well and cells were washed 34 times very gently with PBS for. Fresh media was added to the wells and incubated for another 10 hrs. Images of the wounds were taken at time of point of 12 h, 14 h, 16 h and 18 h of incubation. Analyses of the images were performed using Image J software, and the percentage of wound healing was calculated.

Results

Figure 9:
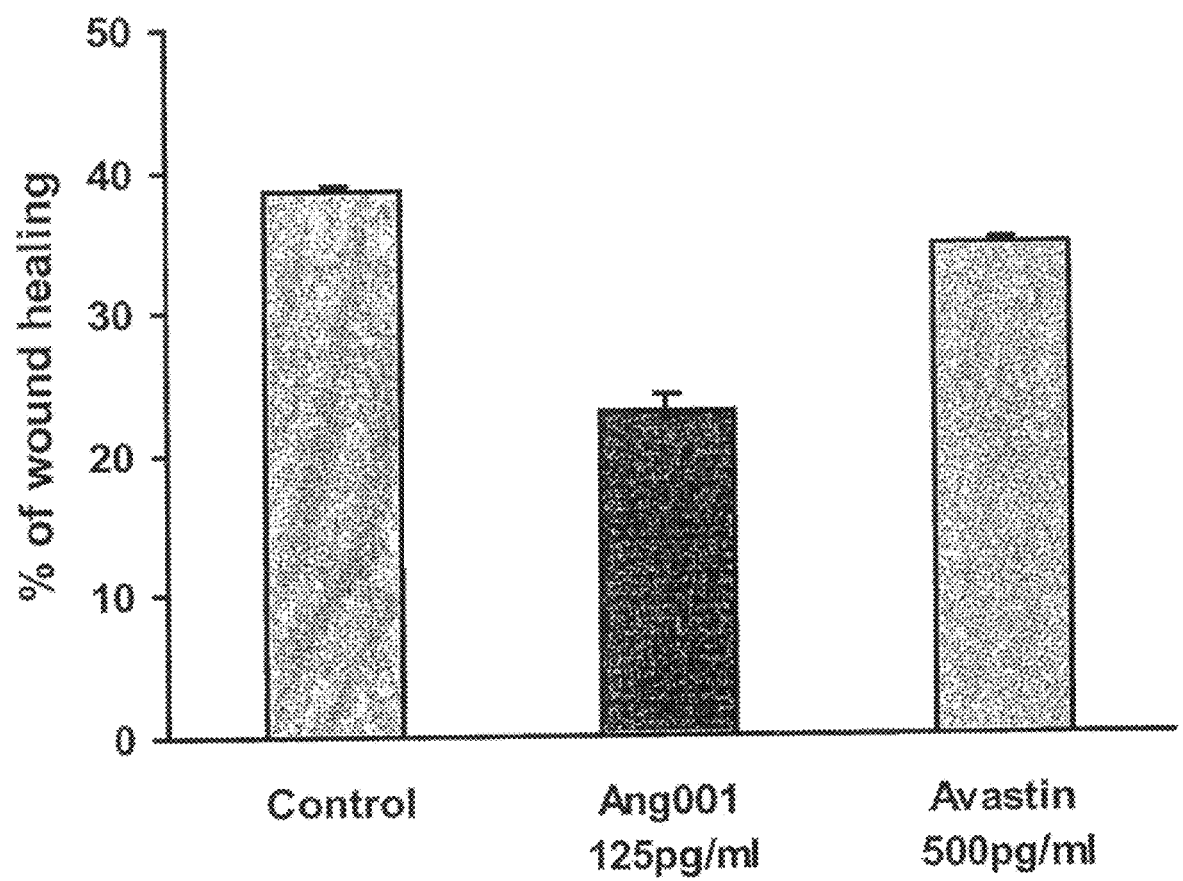
FIG. 9—Depicts results from a scratch wound assay with Avastin and sFRP-4. To check the relative effect of sFRP-4 and Avastin, wound healing assay was performed with sFRP-4 and Avastin. Result suggest that sFRP-4 even in lower concentration was more potent than Avastin in blocking wound healing. (n=5). **Significantly different from control set. ($p<0.001$). *Difference from control was statistically significant. ($p<0.05$)

Results suggest that sFRP-4 (125 pg/ml) is more potent that Avastin (500 pg/ml) in blocking wound healing (see FIG. 9).

EXAMPLE 9 sFRP-4 Inhibits Blood Vessel Formation

Materials/Methods

Fourth day fertilized and incubated chicken eggs were collected from the Poultry Research Station, Nandanam, Chemai. Eggs were broken and gently plated on a cellophane bed in Petri dishes under sterile conditions. Sterile filter paper discs soaked in different concentrations of (0, 125, 250 and 500 pg/ml) of sFRP-4 were placed on the egg yolks. Egg yolks were incubated for 12 hours at 37° C./5% $CO_2$. Images were taken using an Olympus stereo microscope equipped with Nikon digital camera at 0 h, 6 h and 12 h of incubation. Quantification of angiogenesis was performed by using image processing software; Image J, Release Alpha 4.0 3.2 and Adobe Photoshop version 7.0.

Results

Figure 10A:
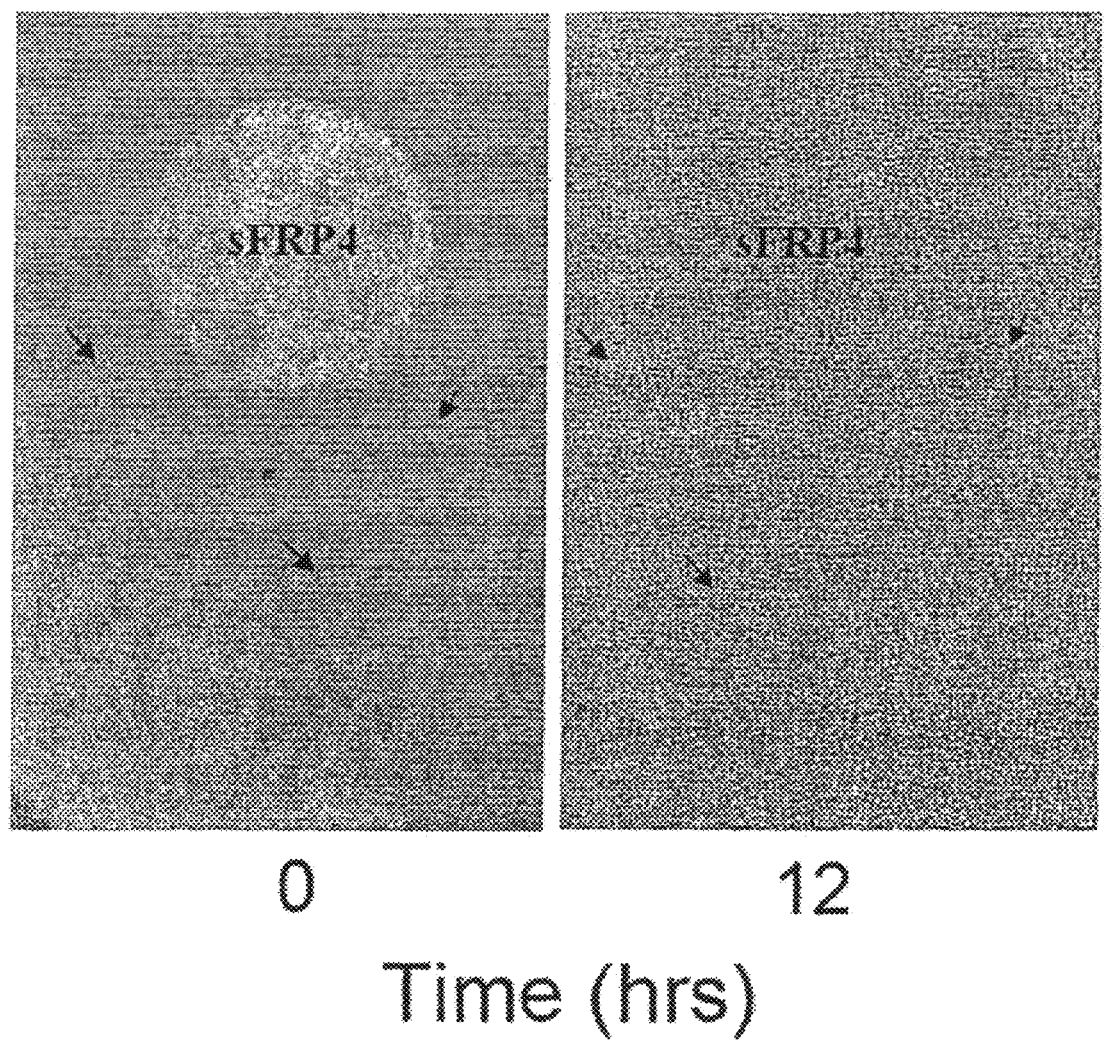
FIG. 10A—Image showing ability of sFRP-4 to inhibit blood vessel formation in egg yolk assay. Egg yolk angiogenesis assay was performed to check the effect of sFRP-4 on the egg yolk vascular bed. Blood vessel formation was inhibited following sFRP-4 treatment. In addition, it was also observed that sFRP-4 to some extent destroys preformed blood vessels.
Figure 10B:
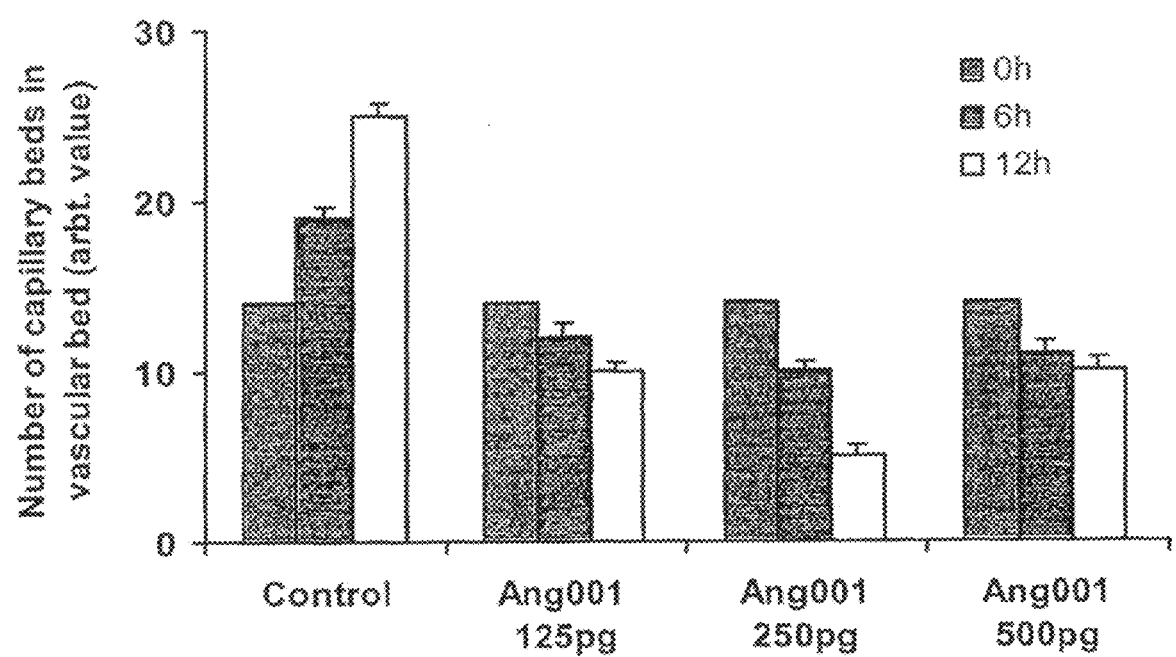
FIG. 10B—Graph quantifying the results in FIG. 10A. Graph was plotted by counting the number of blood vessels following sFRP-4 treatment. Blood vessel count decreases under sFRP-4 treatment. (n=3). *Difference from control was statistically significant. ($p<0.05$)

FIGS. 10A and 10B depict that the number of blood vessels in the egg yolk vascular bed has come down by 70% under sFRP-4 treatment.

EXAMPLE 10

Cotton Plug Method—In Vivo Assay

Materials/Methods 10-20 mg of sterile absorbent cotton (Araiwa Co; Japan, model No. 8) was used to prepare plugs. A stock concentration of 50 ng/ml was prepared using sterile MilliQ water. 50 µl of solution containing 125 pg of sFRP-4 and another 50 µl of solution containing 250 pg of sFRP-4 were prepared from the main stock. The 50 µl solution containing 125 pg and 250 pg respectively were then soaked in cotton plugs. Rats were anesthetized using chloroform. A small incision was created in dorsum to implant cotton plugs subcutaneously. After implantation, wounds were sutured. After 7 days of incubation rats were sacrificed and resulting granulomas were removed surgically. Close up photographs of granulomas with adjacent skin layers were taken using Cannon Coolpix digital camera. The tissue samples were kept in physiological saline overnight on a rocking platform (10 rpm), which allowed leaching out of haemoglobin in the saline. Haemoglobin was measured by measuring the OD of the haemoglobin containing saline at 532 nm. All the containing saline at 532 nm. All the values of haemoglobin concentrations were normalized against the weight of the granulomas. Methods were carried out according to Ajoy Kumar Ghosh, et al (2002) (Ajoy Kumar Ghosh, Noriyasu Hirasawa, Hiroshi Ohtsu, Takehiko Watanabe, and Kazuo Ohuchi (2002) Defective Angiogenesis in the Inflammatory Granulation Tissue in Histidine Decarboxylase-deficient Mice but not in Mast Cell-deficient Mice J Exp. Med. 195, 973-982)

Results

Figure 11A:
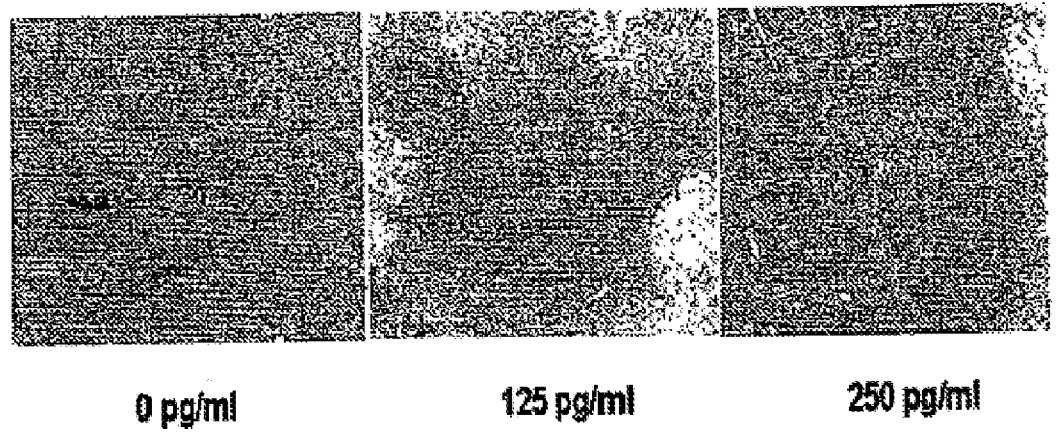
FIG. 11A and FIG. 11B—Depicts results from in vivo cotton plug assays using sFRP-4. In vivo angiogenesis assay was performed using different models following sFRP-4 treatment.
Figure 11B:
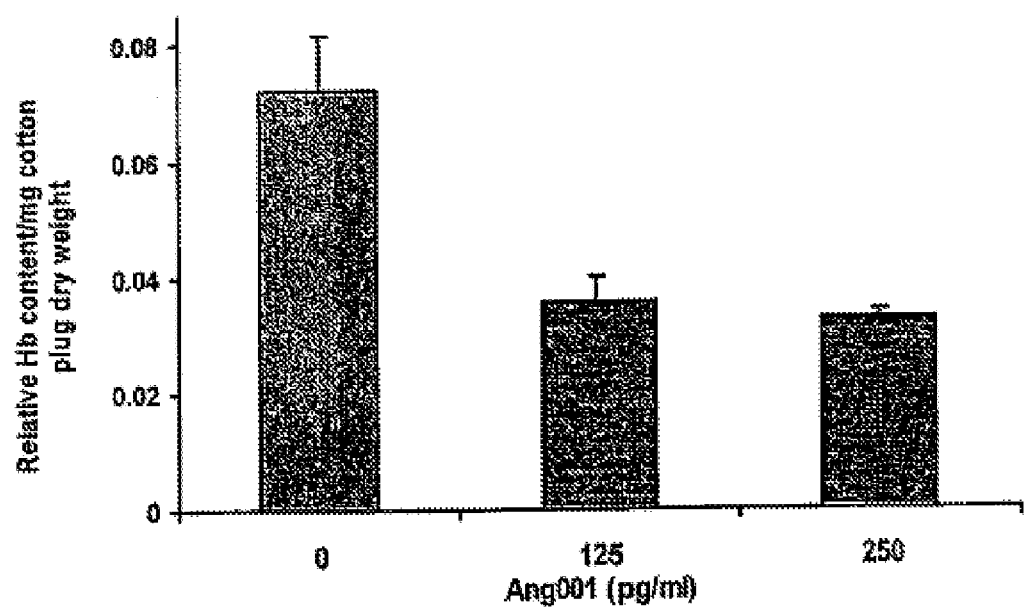

Images acquired from the experiments show that sFRP-4 treated implanted cotton pellets block the entry of blood vessels in the pellets. As Hb content represents the volume of blood vessels in a system, these results prove that sFRP-4 restricts blood vessel entry into the pellets (see FIG. 11A and FIG. 11B).

EXAMPLE 11

Matrigel & Sponge Assay—In Vivo Assay

Materials/Methods

Matrigel (stored at −20° C.) was thawed at 4° C. over night. 0.5 ml of matrigel was dispensed to Eppendorf tubes in ice. sFRP-4 stock of 50 ng/ml was prepared using sterile milliQ water. SFRP-4 from the 50 ng/ml stock was added to 0.5 ml of matrigel in such a way that final SFRP-4 concentration will be 125 pg and 250 pg respectively. 0.5 $cm^2$ samples of sponges (Amersham Bioscience cat No. 80-6206-92) were prepared and sterilized under UV for 1 h. Matrigel/sFRP-4 solution was soaked on to sponge. After soaking, those sponges were incubated at 37° C. for 2 h in order solidify the matrigel. Rats were anaesthetised using chloroform. A small incision was created in dorsum and the sponge containing matrigel was subcutaneously implanted in rats. Following implantation, wound was stitched. After 8 days rats were sacrificed and the resulting granulomas were removed and close up photographs were taken as described previously. The tissue samples were kept in saline for 3-4 hrs for haemoglobin measurement.

For histopathology, tissue samples were processed with 4% paraformaldehyde prepared in Phosphate buffer (pH 7.2). Freshly made paraformaldehyde was used for fixing tissue sample. Ratio of tissue sample-paraformaldehyde was 1:4.

Paraformaldehyde was prepared according to the following method: 4 g of powdered paraformaldehyde was added to 50 ml of 0.2M buffer (pH 7.4), and heated to 65° C. with constant agitation. The resultant solution was cloudy. A few drops of 1N NaOH, was added with constant stirring, until the solution became clear. The solution was allowed to cool and was then made up to 100 ml with distilled water. The fixative contained 4% paraformaldehyde in 0.1M buffer. The fixative was prepared and stored in a clean bottle (Ref: Fixation, Dehydration and Embedding of Biological Specimens Practical Methods in Electronic Microscopy (Paperback) by Glauert Audrey M, North Holland Publishing Co. (1991).

Method of preparation of 0.2M Phosphate Buffer: (preparation was according to the method of Sorensen, see Dawson et al 969 (Studies on tetanus toxin and toxoid. 3. Sedimentation of toxin and derivatives obtained by sulphite and aldehyde treatments. Dawson D J, Nichol L W., Aust J Biol Sci. 1969 February; 22 (1):247-55). To obtain a pH 7.4 mix 40.5 ml of a dibasic sodium phosphate with 9.5 ml of a monobasic sodium phosphate. The method was performed in accordance with Akhtar et al. The Sponge matrigel Angiogenesis Assay; Angiogenesis November 2004, at the url on the world wide web of springerlink.com/content/mn68814h331x4613/; Hassan et al. Quantitative Angiogenesis Assay Invivo-A review; Angiogenesis November, at the url on the world wide web of springerlink.com/content/m04t2n7910h3h634/; and Scapini et al. Journal of Immunology; at the url on the world wide web of jimmunol.org/cgi/reprint/172/8/5034).

Results

Figure 12A:
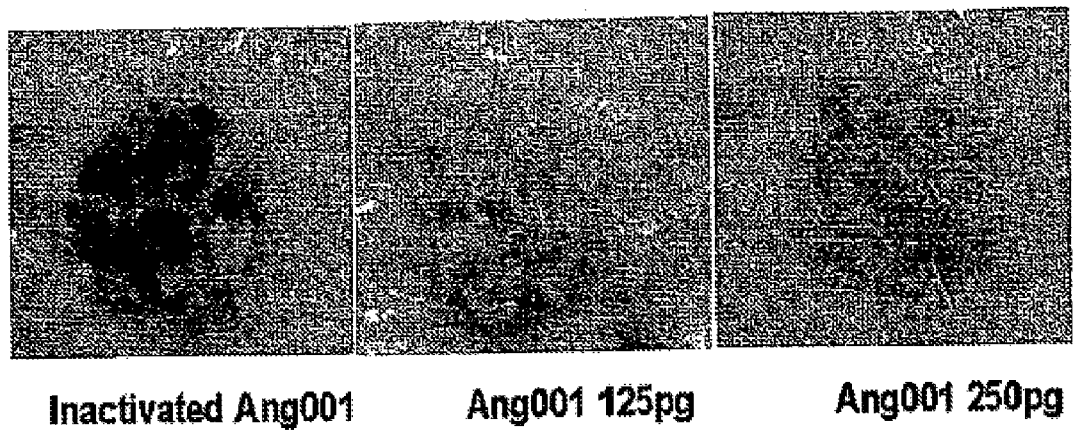
FIG. 12A and FIG. 12B—Depict results from in vivo spongemat assays using sFRP-4. Spongemat assay was performed using matrigel as a matrix to which blood vessels can invade while sponge was acting as a scaffold material for the matrigel.
Figure 12B:
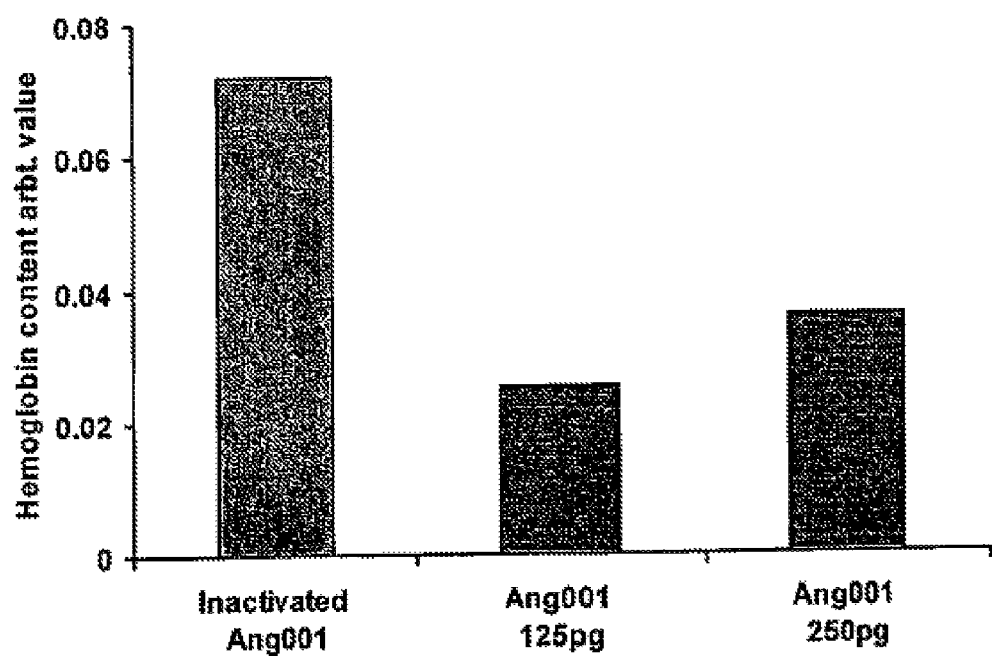

Images acquired from the experiments show that sFRP-4 inhibits blood vessel formation. Assay of Hb content of the pellets reveals that sFRP-4 treated sets contain less Hb. The results of these two experiments suggest that sFRP-4 block blood vessel formation in in-vivo angiogenesis model (see FIG. 12A and FIG. 12B).

EXAMPLE 12

Matrigel Assay—In Vivo Assay

Materials/Methods

Matrigel (stored at −20° C.) was thawed at 4° C. over night. 0.5 ml of matrigel was dispensed to Eppendorf tubes in ice. SFRP-4 stock of 50 ng/ml was prepared using sterile MilliQ water. sFRP-4 from the 50 ng/ml stock was added to 1 ml of matrigel in such a way that final sFRP-4 concentration will be 125 pg and 250 pg respectively. 6 week old mice were anesthetized using chloroform. Matrigel containing sFRP-4 was transferred to 1 ml syringes and then injected subcutaneously in between upper left groin and sternum. Mice were sacrificed after 7 days, and gels were removed surgically. Close-up photographs of gels with adjacent skin layers were taken by using. Cannon Coolpix digital camera. The matrigel pellets were then processed for haemoglobin estimation and histopathology. Matrigel samples were kept in physiological saline overnight on a rocking platform (10 rpm), which allowed leaching out of haemoglobin in the saline. Haemoglobin was measured by taking OD of the haemoglobin containing saline at 532 nm. All the values of haemoglobin concentrations were normalized against the weight of the granulomas.

For histopathology tissue sample was processed with 4% paraformaldehyde made in Phosphate buffer (pH 7.2). Freshly made paraformaldehyde was used for fixing tissue sample. Ratio of tissue sample:paraformaldehyde was 1:4. The methods were performed according to Disorder Cellular Migration and Angiogenesis in cd39-Null Mice Goepfert et al., Circulation Research, 2001; Angiogenesis Assay: A critical Overview; Auerbach et al; Clinical Chemistry, 2003 BD-Bioscience, at the url on the world wide web of bdbiosciences.com/discovery.labware/technical_resources/pdf/TB455.pdf).

Results

Figure 13:
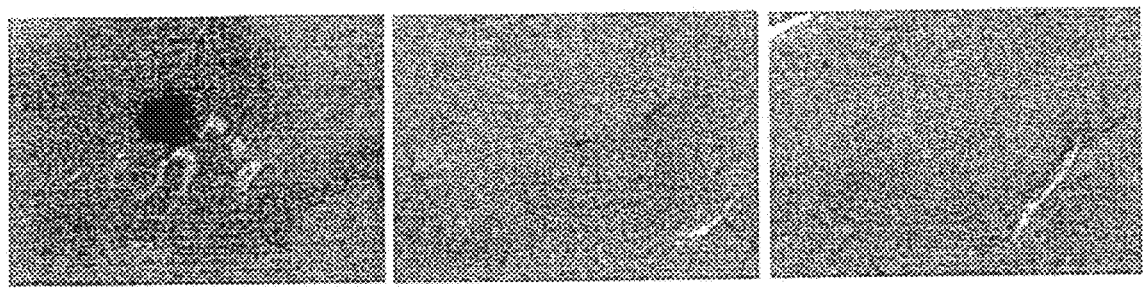
FIG. 13—Depicts results from in vivo matrigel plug assays using sFRP-4. Matrigel plugs were used to determine the effect of sFRP-4 on neovasculogenesis in mice. Images taken of the plug showed clear inhibition of blood vessel formation. (n=2)

Images acquired from the experiments show that sFRP-4 inhibits blood vessel formation in implanted matrigel plugs, an in-vivo angiogenesis model (see FIG. 13).

EXAMPLE 13

Construction of CRD and Netrin-Carboxy Terminal Fragments from Human sFRP4

Materials/Methods

*Homo sapiens* secreted frizzled-related protein 4 was obtained from accession No. DQ420628. pDEST12.2 was used as the source clone for sFRP4. pDEST12.2 contained the sFRP4 sequence under the control of the CMV promoter.

The construction was performed with PCR employing high fidelity enzyme using the Clontech peGFP-N1 vector such that the full length sFRP4 coding and Kozak sequences, the CRD domain (SEQ ID NO: 11) or the Netrin carboxy terminal (SEQ ID NO: 12) domain could be expressed amino terminal to the GFP in frame as fusion proteins (SEQ ID NO: 10). Both CRD and the Netrin retained the Kozak and signal sequences of sFRP4.

Amino acids 1-18 were signal sequence. The CRD construct expressed the signal sequence followed by AA 19 until 144, then adds a proline and continues in frame with GFP (SEQ ID NO: 13).

The Netrin construct takes advantage of an Asc I restriction site to retain the coding sequence from amino acid 1 until AA 23, followed by sequences encoding amino acids 178 until 346 continuing in frame with GFP (SEQ ID NO: 14).

Construction of the eGFP N1 Subclones:

Full-Length sFRP4 was Cloned in Frame (and without the Stop Codon) in N1 peGFP as Follows:

A high fidelity PCR reaction was performed with the following 2 primers:

```
Sense:                                    (SEQ ID NO: 3)
5'-CAC AGG AAA CAG CTA TGA CC-3'

Anti-sense:                               (SEQ ID NO: 4)
5'-GCT GGA TCC CAC ACT CTT TTC GGG T-3' (contain-
ing a BamHI site which destroys the stop codon of
sFRP4).
```

For the 5' end of the construct, an internal sFRP4 KpnI site at nucleotide -46 (that means 46 nucleotides 5' (upstream) from the initiating atg) of the dDEST12.2 sFRP4 was used. After restriction this site was conveniently ligated into a KpnI site in peGFP N1 (SEQ ID NO: 10). BamHI restriction provided a 3' end (lacking a stop codon) which could be ligated in frame into the polylinker BamHI site of N1 peGFP (SEQ ID NO: 10).

Between the sFRP4 peGFP N1 sequences is a short sequence of 7 amino acids (WDPPVAT (SEQ ID NO: 9)—including two prolines for a bend) added with the PCR primers and N1 sequence ahead of eGFP (SEQ ID NO: 10).

The signal sequence+Cystein Rich Domain subclone was prepared as follows:

A PCR reaction was performed using the following 2 primers:

```
Sense:                                    (SEQ ID NO: 5)
5'-CAC AGG AAA CAG CTA TGA CC-3';

Anti-sense:                               (SEQ ID NO: 6)
5'-ATC CTC CGG GGG ATC CGT GAC GAT G-3' (contain-
ing a BamHI site)
```

For the 5' end of the construct, an internal sFRP4 KpnI site at nucleotide –46 (that means 46 nucleotides 5' (upstream) from the initiating atg) of the dDEST12.2 sFRP4 was used. This site was conveniently ligated into a KpnI site in peGFP N1.

To define the 3' end of the CRD sequences, a BamHI site was incorporated into the primer, which after restriction could be ligated in frame into the BamHI site in the polylinker ahead of the N1 eGFP sequences.

After the sFRP4 the N1 eGFP sequence was fused in frame at the same BamHI site used with the wild type (SEQ ID NO:13).

The signal sequence (AA 1-23)+netrin carboxy end domain was prepared as follows:

The 5' end of the plasmid was obtained by restricting the full-length sFRP4 N1 peGFP with AscI and BamHI. To this linearized plasmid was ligated the following PCR fragment defined with primers.

```
Sense:                                    (SEQ ID NO: 7)
5'-GAC TGT AAA GGC GCG CCC CCC GAT CGG TGC AAG-3'
(containing an AscI site).

Anti-sense:                               (SEQ ID NO: 8)
5'-GCT GGA TCC CAC ACT CTT TTC GGG T-3' (contain-
ing a BamHI site which destroys the stop codon of
sFRP4).
```

After restriction with AscI and BamHI, the PCR fragment was ligated into the linearized N1 plasmid which already contains the signal sequence of sFRP4 up to the internal AscI site.

After AA 346 the N1 eGFP was fused in frame using the same BamHI site and transitional sequence (SEQ ID NO:14).

Results

The resulting constructs were sequenced to establish in frame. Immunoprecipitation has shown the 3 different sized fusion proteins as products following expression in cell culture (see FIG. 14).

EXAMPLE 14

Matrigel Tube Formation Assay

Materials/Methods

130 µl of diluted matrigel (matrigel conc. 8 mg/ml) was placed in wells of a 24 well plate and incubated at 37° C. for 20 mins. Once the matrigel became hard transfected ECV cells (transfected with SFRP-4, Netrin, CRD and N1 vector as control) were seeded on to it. Seeded cells were incubated in $CO_2$ incubator for 48 hrs at 37° C. Next, two end-points were counted from the wells by using Nikon Inverted microscope under 20× objective. 1) Number of tubes formed 2) number of tubes with or without collaterals.

Results

Figure 15:
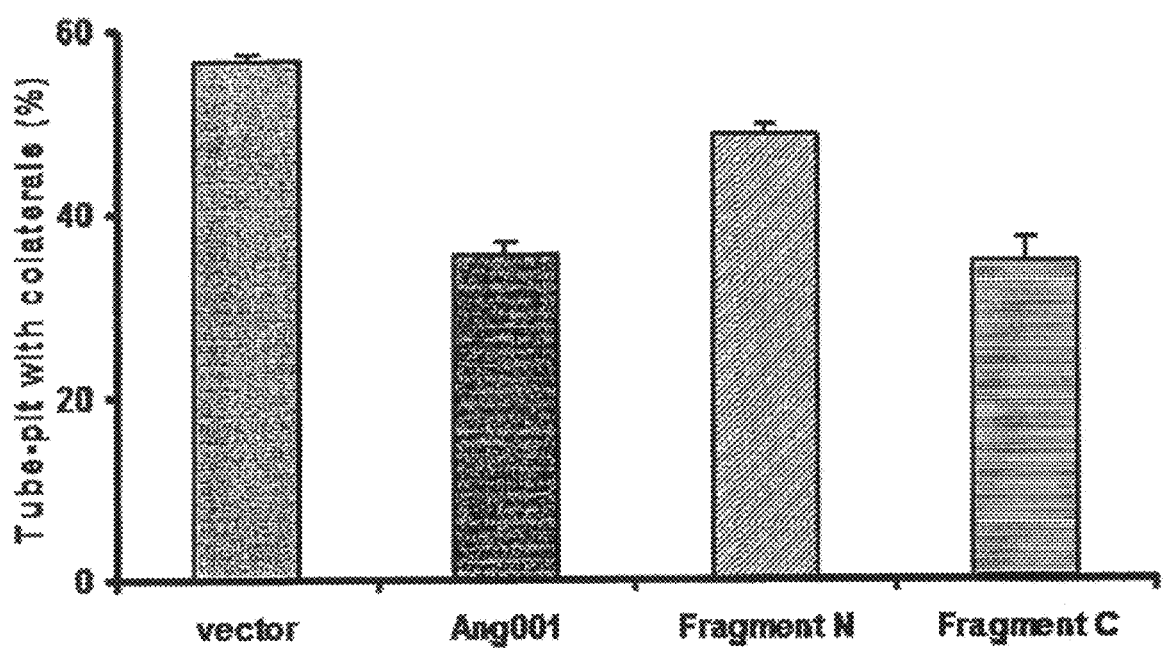
FIG. 15—Depicts results from matrigel collateral formation assays using sFRP-4 and various FRP-4 fragments. Transfected cells were used to check the conduits and collateral formation by the conduits. Number of collateral positive conduits was counted and plotted. Results suggest inhibition of collaterals formation under sFRP-4 and CRD vector transfected cells. (n=5). *Statistical analysis showed significant difference from control group. (p<0.05)

Collaterals from the endothelial or isolated aorta rings are functional representative of angiogenesis. Results from this experiment suggest that cells transfected with sFRP-4 and CRD vector are less capable of forming tubes and collaterals than N1 (control) and Netrin vector transfected cells (see FIG. 15)

EXAMPLE 15

Transfection of Cells Using Lipofectin

Materials/Methods

ECV 304 cells were seeded 24 hrs before transfection. 5 ug of DNA (Netrin, CRD, SFRP-4, N1 vector) was diluted in 100 ul of media (DMEM from Invitrogen Inc. Cat No. 12430-054) without serum (Fetal Bovine) and antibiotics, penicillin and streptomycin (solution A). 10 ul of lipofectin reagent was added to 100 ul media without serum and antibiotic and incubated for 30 min (solution B) at room temperature. Both the solutions A and B were mixed and incubated for 10-15 min at room temperature (solution C). The media was removed from the dish. Dishes were washed two times with media without serum and antibiotic. 0.8 mL of media without serum and antibiotic was added to the solution C. 200 ul of the solution C was added to each well of a 24 well plate. Cells were incubated at 37° C. in $CO_2$ incubator for 12 hours. Media was replaced with fresh media containing serum and antibiotic. The cells were further incubated at 37° C. in $CO_2$ incubator for 36 hours. Expression of the GFP tagged proteins was detected by fluorescence microscope.

Results

Figure 16:
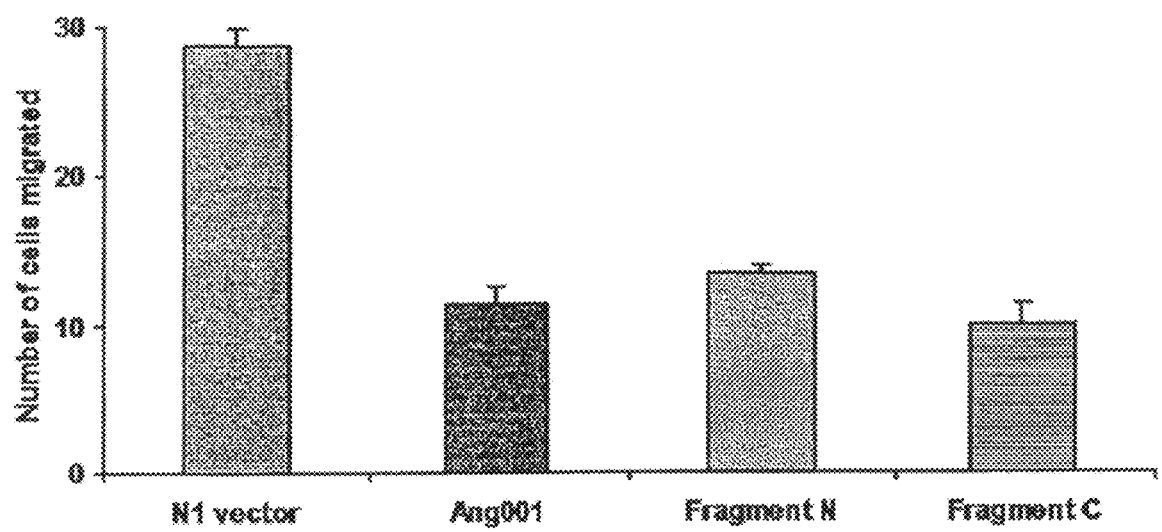
FIG. 16—Depicts migration assay results from transfection of cell with lipofectin, using sFRP-4 and various FRP-4 fragments as treatments. Boyden's chamber migration assay was performed using the transfected cells. sFRP-4 and CRD have less migratory property than of netrin and N1 vector transfected cells. (n=7) *Significantly different from control group. (p<0.05)
Figure 17:
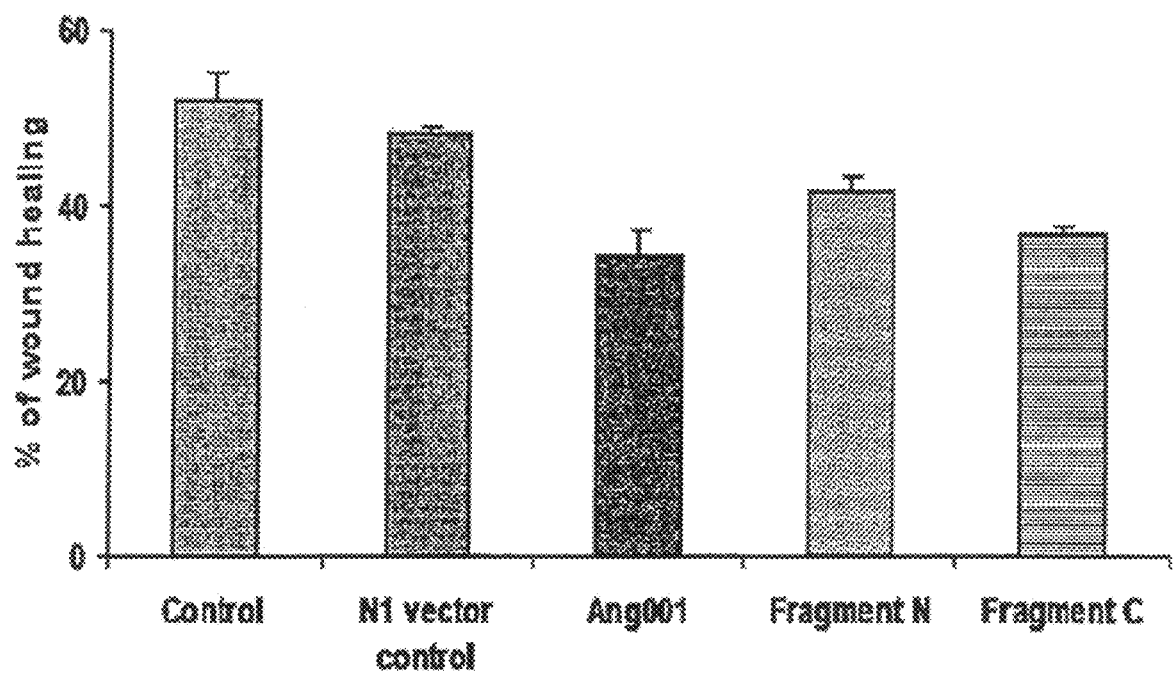
FIG. 17—Depicts wound healing assay results from conditional media experiments using sFRP-4 and various FRP-4 fragments. Conditional media from transfected cells were used to investigate the wound-healing pattern of ECV304 cells. Conditional media from sFRP-4 and CRD transfected cells inhibited wound healing of ECV304 cells. (n=5) *Difference from control was statistically significant. (p<0.05)

After transfection cells were observed under microscope for the green fluorescence. Cells showing green fluorescence suggest that cells were transfected with different vectors (Netrin, CRD, sFRP-4 and N1) tagged with Green Fluorescent protein (GFP). These transfected cells were then used for different experiments such as migration (see FIG. 16), wound healing (see FIG. 17) and tube formation (see FIG. 15) assay.

EXAMPLE 16

Conditional Media Experiment

Materials/Methods

ECV304 Cells were transfected with N1, Netrin, CRD and SFRP-4 vector. After 12 h of transfection conditional media from transfected cells was collected. The conditioned media was added to the monolayer of ECV304 cells with scratched "wounds". Images of the wounds were taken at the 0 hr and 8 hr. Percentage of wound healing was measured from the images by using Image J and Adobe Photoshop software.

Results sFRP-4 is a secretary protein. Conditioned media from the cells transfected with sFRP-4 and other vectors were collected. When endothelial cells were incubated with conditioned media, SFRP-4 and CRD media blocked wound healing in endothelial cell monolayers. The results indicate that CRD domain has the anti-endothelial property (see FIG. 17)

EXAMPLE 17

Identification of an Endothelial Cell Receptor for sFRP-4

Materials/Methods

Yeast two-hybrid screening will be performed with components of the matchmaker 20Hybrid System 2 (Clontech). The C-terminal domain of sFRP-4 will be cloned by polymerase chain reaction into pAS2-1 (Clontech), and the resulting construct will be verified by sequencing. The PJ69 reporter yeast strain will be transformed with a bait construct using previously published method and autoactivation will be excluded by transformation with empty library vector. The 2-hybrid screen will be performed using a library from phytohaemagglutinin stimulated leukocytes (Clontech, cat #HL4021AB) with bacterial RNA as carrier nucleotides. For primary selection, colonies will be grown on media lacking leucine, tryptophan, and adenine (selecting for the presence of both bait and prey plasmids and for the interaction between bait and prey proteins). Positive clones will be transferred to quadruplicate selection plates (also lacking histidine) and will be tested for beta-galactosidase activity. Yeast DNA will be prepared by the method described previously, followed by electrotransformation into HB101 bacteria and sequence analysis of lacZ-positive interaction partners.

The endothelial receptors(s) identified as sFRP-4 binding partner(s) above will be used subsequently in complimentary immunoprecipitation experiments, to further demonstrate specific binding interactions. The sFRP-4 cDNA will be subcloned into pcDNA3.1/myc-His and the endothelial receptor protein(s) cDNA will be subcloned into pcDNA3.1/V5-His. These vectors and anti-myc/anti-V5 precipitating monoclonal antibodies can be obtained from in vitrogen. NIH 3T3 mouse mesenchymal cells will be transiently co-transfected with both plasmids, which encode epitope-tagged sFRP-4 and receptor protein. In control experiments, cultures will be transfected with only one plasmid or empty vectors. Epitope-tagged proteins will be expressed 24-48 hours and then (a) immunoprecipitated from media and cell lysates using anti-myc and anti-V5, separately; (b) size-fractionated on denaturing and non-denaturing PAGE gels; (c) immunoblotted with anti-sFRP-4 IgG. If sFRP-4 and the expressed receptor protein bind specifically, they should co-precipitate with the anti-myc and anti-V5 monoclonals and be detected by immunoblotting the precipitates with anti-sFRP-4 IgG. Angiogenic assays will be used to determine if the expressed proteins induce anti-angiogenic effect.

Modifications of the above-described modes of carrying out the various embodiments of this invention will be apparent to those skilled in the art based on the above teachings related to the disclosed invention. The above embodiments of the invention are merely exemplary and should not be construed to be in any way limiting.

We claim:

1. A method for inhibiting angiogenesis in a mammalian tissue of a subject afflicted with a disease or disorder associated with undesirable levels of angiogenesis, comprising the step of: administering Secreted Frizzled-related Protein-4 (sFRP-4) to the tissue, wherein said sFRP-4 comprises an amino acid sequence with at least 95% sequence identity to SEQ ID NO:1 or SEQ ID NO:2; wherein said sFRP-4 is anti-angiogenic, and wherein administering said s-FRP4 inhibits angiogenesis in said tissue.

2. The method of claim 1, wherein said sFRP-4 protein comprises the amino acid sequence of SEQ ID NO:1.

3. The method of claim 1, wherein said sFRP-4 protein comprises the amino acid sequence of SEQ ID NO:2.

4. The method of claim 1, wherein said disease or disorder associated with undesirable levels of angiogenesis is cancer.

5. The method of claim 1, wherein said disease or disorder associated with undesirable levels of angiogenesis is age related macular degeneration.

* * * * *